US008506799B2

(12) United States Patent
Jorden et al.

(10) Patent No.: US 8,506,799 B2
(45) Date of Patent: Aug. 13, 2013

(54) SUSPENDED PARTICLE CHARACTERIZATION SYSTEM FOR A WATER PROCESSING FACILITY

(75) Inventors: Roger M. Jorden, Longmont, CO (US); John W. English, Boulder, CO (US); Daniel J. Bodenstein, Boulder, CO (US)

(73) Assignee: ClearCorp, Longmont, CO (US)

( * ) Notice: Subject to any disclaimer, the term of this patent is extended or adjusted under 35 U.S.C. 154(b) by 751 days.

(21) Appl. No.: 12/556,517

(22) Filed: Sep. 9, 2009

(65) Prior Publication Data

US 2011/0060533 A1 Mar. 10, 2011

(51) Int. Cl.
*C02F 1/52* (2006.01)
(52) U.S. Cl.
USPC .......... 210/94; 210/85; 210/95; 210/143; 210/709; 702/23; 702/25; 702/29
(58) Field of Classification Search
USPC .................................. 210/709, 85
See application file for complete search history.

(56) References Cited

U.S. PATENT DOCUMENTS

| | | | |
|---|---|---|---|
| 4,170,553 A | 10/1979 | Lang et al. | |
| 4,282,093 A | 8/1981 | Haga et al. | |
| 4,654,139 A * | 3/1987 | Baba et al. ............. | 210/85 |
| 4,661,845 A * | 4/1987 | Saito et al. ............. | 348/81 |
| 4,752,131 A | 6/1988 | Eisenlauer et al. | |
| 4,783,269 A * | 11/1988 | Baba et al. ............. | 210/709 |
| 4,855,061 A | 8/1989 | Martin | |
| 4,867,886 A | 9/1989 | Botkins, Jr. | |
| 4,950,908 A | 8/1990 | Oblad et al. | |
| 5,194,921 A | 3/1993 | Tambo et al. | |
| 5,360,549 A * | 11/1994 | Mouche et al. ............. | 210/696 |
| 5,376,280 A | 12/1994 | Wilhelm et al. | |
| 5,380,440 A | 1/1995 | Chipps | |
| 6,171,480 B1 * | 1/2001 | Lee et al. ............. | 210/85 |
| 7,037,433 B2 | 5/2006 | Abu-Orf et al. | |
| 7,303,685 B2 | 12/2007 | Clark | |
| 7,609,297 B2 * | 10/2009 | Master et al. ............. | 348/222.1 |
| 7,758,696 B2 * | 7/2010 | Stoddard et al. ............. | 117/52 |
| 7,910,004 B2 * | 3/2011 | Cohen et al. ............. | 210/652 |
| 2009/0208582 A1 * | 8/2009 | Johnston et al. ............. | 424/489 |

OTHER PUBLICATIONS

Alessandra Mantovanelli, Peter V. Ridd, "Devices to measure Setting Velocities of Cohesive Sediment Aggregates: A Review of the In Situ Technology"; James Cook University, School of Mathematics and Physics, Townsville, Australia, Accepted May 16, 2006, 1 page.
Sedvel, "An Underwater Balance for Measuring In Situ Settling Velocities and Suspended Cohesive Sediment Concentrations," James Cook University, School of Mathematics and Physics, Townsville, Australia, Accepted Oct. 2, 2008, 1 Page.

(Continued)

*Primary Examiner* — Tony G Soohoo
*Assistant Examiner* — Peter Keyworth
(74) *Attorney, Agent, or Firm* — Kilpatrick Townsend & Stockton LLP

(57) ABSTRACT

A system for characterizing suspended particles in a water treatment facility is disclosed. The system uses an imaging array to take multiple images of the particles in a sample volume. These images are then processed to determine geometrical properties of individual particles in the sample. These geometric properties can then be used to identify properties of the sample volume such as particle volume concentration, particle number concentration, computed particle diameter, gravitational settling velocity, mass concentration, and computed particle volume.

21 Claims, 25 Drawing Sheets

(56) References Cited

OTHER PUBLICATIONS

Jin, Yan, "Use of a High Resolution Photograpic Technique for Studying Coagulation/Flocculation in Water Treatment;" MS Thesis, 2005, University of Saskatchewan; 152 pages.

Jarvis, Peter, Bruce Jefferson and Simon A. Parsons, "Measuring Floc Structural Characteristics," School of Water Sciences, Cranfield University, Cranfield, Bedfordsire, MK43 0AL, United Kingdom; 2005;49 pages.

Alessandra Mantovanelli, "A New Approach for Measuring in situ the Concentration and Settling Velocity of Suspended Cohesive Sediment;" Ph. D. 2005; James Cook University: 214 pages.

Manning, Andrew James and Dyer, Keith Richard, "The Use of Optics for the in situ Determination of Flocculated Mud Characteristics;" 2002, J. Opt. A Pure Appl. Opt. 4 S71-S81, 2 pages.

Ingels, Tyson F., "Optimizing Granular Media Filtration Through Bench Scale and in-situ Floc Particle Characterization;" MS Thesis, 2006; Colorado School of Mines, 165 pages.

CLEARCORP RoboJar Data Sheet © 2005, 5 pages.

CLEARCORP FlocMonitor Data Sheet © 2006, 2 pages.

CLEARCORP On-Line "Jar Testing of Full Process Stream," © ClearCorp Dec. 7, 2005, 5 pages.

Drewes, Jorg E, et al., "State-of-the-Art Floc Particle Characterization—Optimizing Granular Media Filtration," Colorado School of Mines, no date, 1 page.

Ingels, Tyson et al., "Optimizing Filtration Pre-Treatment Processes Through State-of-the-Art Floc Particle Characterization," AWWA Water Quality Technology Conference, Quebec City, 2005, 33 pages.

Hartog, N., Griffioen, J., Kleingeld, P.J., "Fluidized-Bed Reactor to Study Physico-Chemical Kinetics in Heterogeneous Soils and Sediments," 2002 Doctoral Dissertation avaliable from Utrecht University in the Netherlands.

* cited by examiner

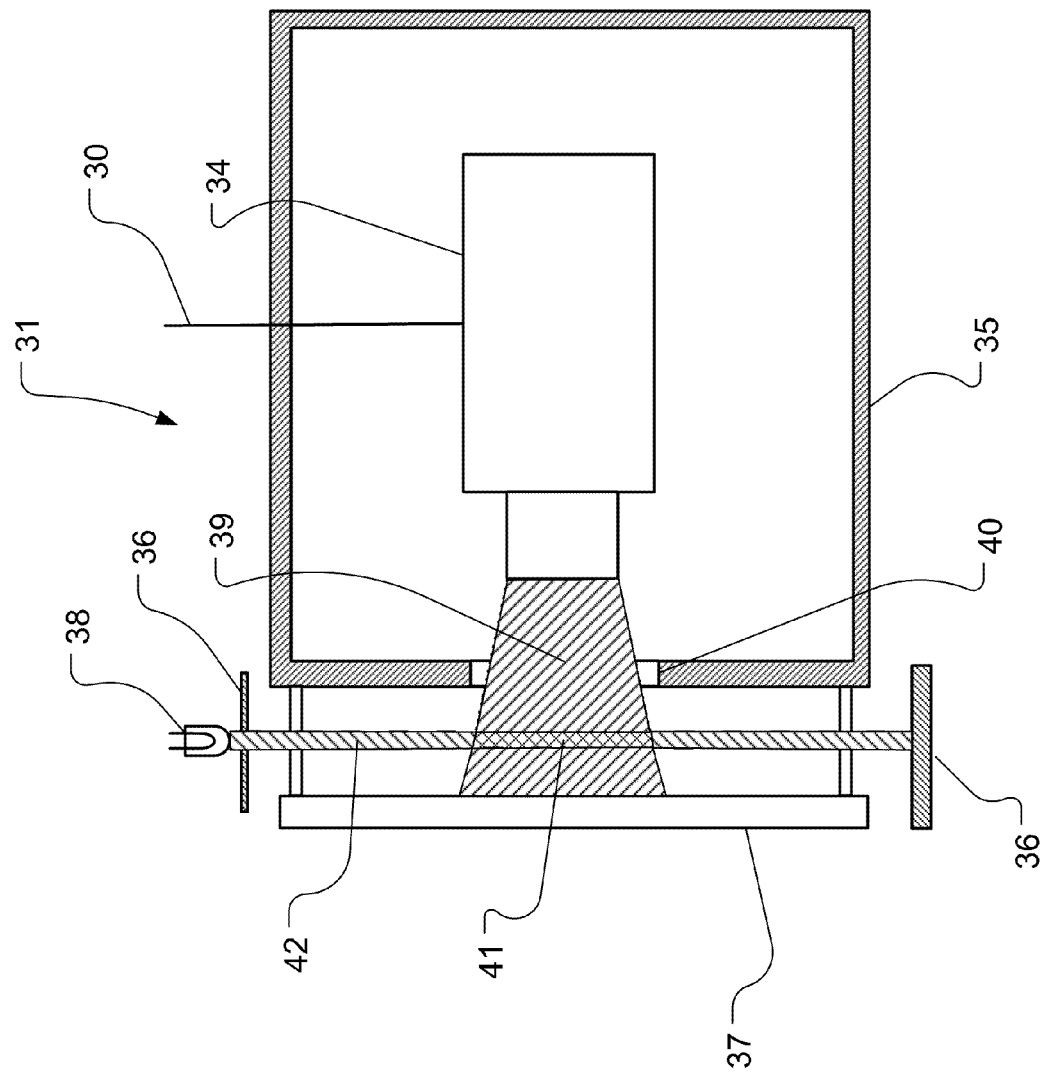

| | | A | B | C | 200 D | E |
|---|---|---|---|---|---|---|
| | Shape | Circumscribed | Heywood | Pappus | Hydraulic | Heywood-Hydraulic |
| I |  | 183 | 156 | 167 | 36 | 96 |
| II |  | 519 | 197 | 173 | 23 | 110 |
| III |  | 721 | 178 | 130 | 34 | 106 |
| IV |  | 526 | 197 | 468 | 29 | 113 |
| V |  | 939 | 197 | 124 | 34 | 115 |
| VI |  | 604 | 224 | 92 | 20 | 122 |
| VII |  | 599 | 180 | 988 | 27 | 104 |
| IIX |  | 360 | 156 | 84 | 19 | 88 |
| IX |  | 100 | 100 | 100 | 100 | 100 |

SUSPENDED PARTICLE CHARACTERIZATION SYSTEM FOR A WATER PROCESSING FACILITY

FIELD OF INVENTION

This invention relates to chemical-physical processing for enhancing the separation of water from dispersed pollutant materials, specifically to a floc particle imaging-processor-communications system for analysis and characterization of coagulation-flocculation system operation as pretreatment for subsequent pollutant-water separation processing such as sedimentation, flotation, granular-media and membrane filtration, as well as sludge dewatering or paper making.

BACKGROUND

Coagulation is the initial make-or-break unit process in water-pollutant separation systems. Flocculation immediately follows coagulation. Combined, coagulation-flocculation represents pretreatment processing for the formation of floc (~mm size aggregates that incorporate pollutants) for their subsequent physical separation. Separation of floc-pollutants is accomplished by a spectrum of large-scale separation process applications spanning from drinking water filtration (granular-media) to membranes and desalting pretreatment, to wastewater treatment, fats-oil-grease removal from industrial wastewater, waste metal and trace element removal, to dewatering including paper making and sludge dewatering.

Coagulation involves chemical addition and dispersion to water that is being treated. Coagulation is remarkably powerful. It can induce 10,000-fold pollutant-particle size changes, and >1,000,000-fold reduction in number concentration of infectious organisms such as the amoeba Cryptosporidium. Coagulation is also versatile as it may induce removal of a diverse variety of pollutant species including;
   (i) Ions of arsenic, phosphorus, fluorine, and trace metals;
   (ii) Dissolved organics that may form carcinogens;
   (iii) Algae, dead microorganisms, their cellular detritus, and infectious virus, bacteria, amoeba;
   (iv) Particulate matter harboring other pollutants.

However, the successful application of coagulation represents a challenge because coagulation-flocculation effects are manifold, slow to manifest, varied, and are used in a wide range of applications. Most importantly, coagulation-flocculation pretreatment represents the 'big lever' for the plant operators for controlling pollutant-removal performance both quality and quantity (throughput) wise.

Coagulation is instantaneous whereas flocculation nominally requires ~½ hour to several hours in older facilities for dilute suspensions, but only minutes for dense slurries. Nominally, coagulation converts otherwise stable negatively charged pollutant species into neutral 'sticky' bodies that gradually grow in size as a result of particle-particle collisions caused by mild turbulent fluid mixing. A fundamental requirement of coagulant dosing is that the total negative charged demand of water must be met by the positive-charge supplied by the coagulant chemicals, referred to as charge neutral coagulation. Dosing beyond this point may be more costly or counterproductive. Flocculation results in the aggregation of pollutant-coagulant sub-particles into larger and larger, more easily removable, entities, or floc particles that ultimately reach some steady-state size. That observed size depends upon the nature of the mixing regime and floc strength characteristics for a given raw water quality and coagulation chemistry. Mixing intensity control represents the physical means for the plant operators to manipulate floc particle characteristics, for a given coagulation-chemistry regime.

Because the terms coagulation and flocculation are used interchangeably by some, these and related terms require defining as to their meaning as used in this invention disclosure. Coagulation refers to the action of the addition of chemical species that in turn lead to the instantaneous precipitation, adsorption, and destabilization of dissolved and particulate matter. Flocculation refers to the agglomeration or aggregation of the destabilized colloids and precipitates. Coagulation-flocculation refers to the coupled unit processes as a pretreatment system preceding the pollutant-floc separation step(s). The term operationally controllable variables—of coagulation-flocculation processing—refer nominally to coagulant chemical dosing and to flocculation mixing intensity.

SUMMARY

In one embodiment, the present disclosure provides an instrument and method for characterizing suspended particles in a water treatment facility. The instrument takes multiple high-resolution images of suspended particles in a defined sample of water in the treatment facility downstream of a point at which coagulant-chemicals have been added to the water stream. The instrument then analyzes these images to characterize the geometric properties of individual particles. Useful geometric properties of individual particles that can be determined by processing these images can include centroid, area, circularity, position, perimeter, and diameter. Once the characteristics of individual particles are understood and quantified, this data can be aggregated and or looked at in a time-sequential way to understand the properties of the sample volume. Among the properties of interest in the sample volume that can be analyzed in this way are particle volume concentration, particle number concentration, computed particle diameters, gravitational settling velocities, mass concentration, and computed particle volumes. By measuring such water sample properties, the present invention can identify the either the impact of the chemicals that have been added upstream of the instrument to the water flowing through the treatment facility and/or the impact of the flocculation mixing regime in an efficient and cost-effective way.

BRIEF DESCRIPTION OF THE FIGURES

The present disclosure is described in conjunction with the appended figures in which:

FIGS. 2A-B are schematic views showing the outline and construction of a summation of the prior art used in a water treatment process;

In the appended figures, similar components and/or features may have the same reference label. Where the reference label is used in the specification, the description is applicable to any one of the similar components having the same reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

Figure 1:
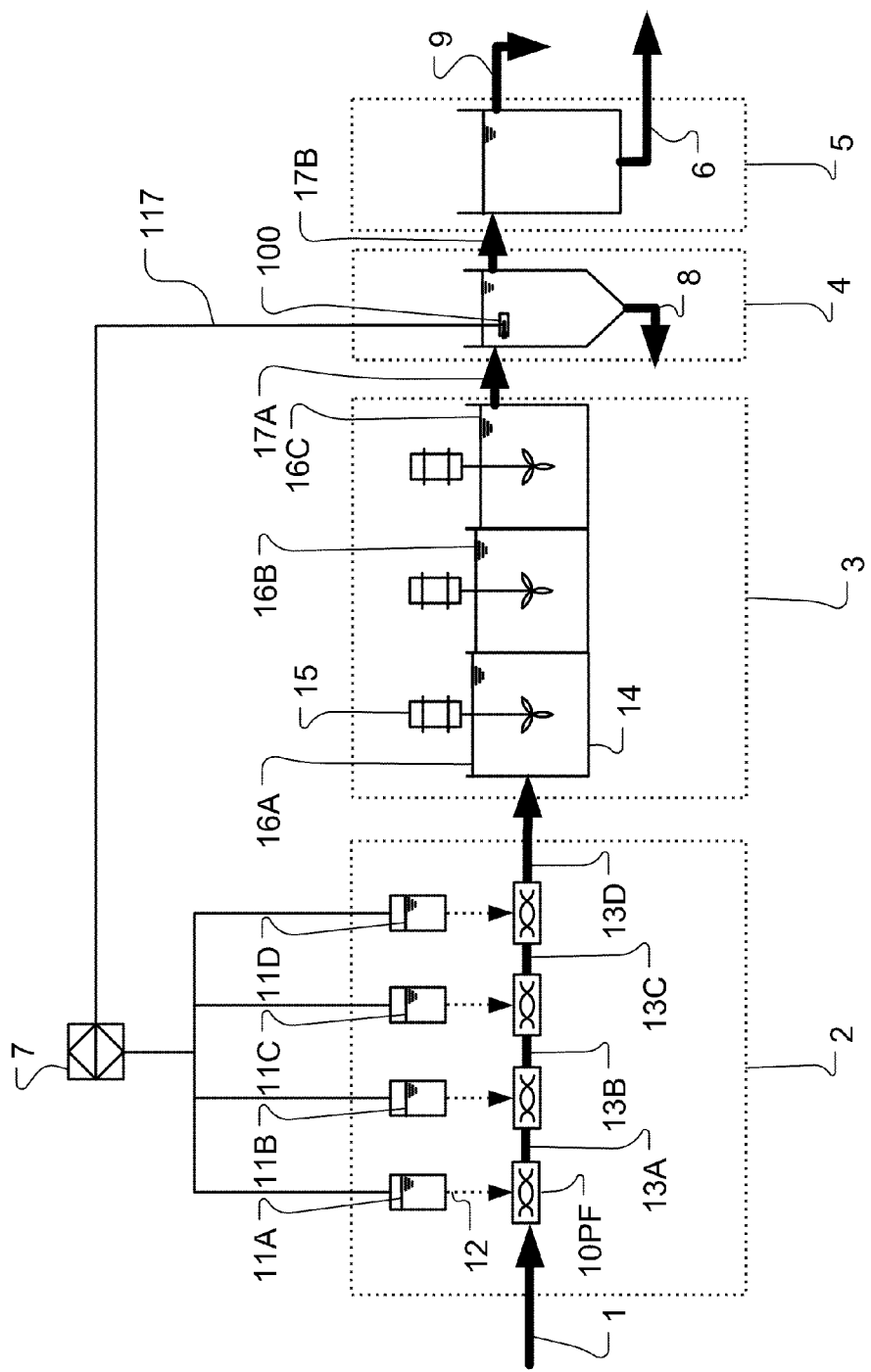
FIG. 1 is a schematic view showing the outline of a pollutant water pretreatment and physical separation process including a clarification basin with an incorporation of one embodiment of the present invention, a suspended particle characterization system.

Referring to a water treatment facility shown in FIG. 1, raw water, shown at 1, is mixed with at least one coagulant chemical species, shown at 11A, 11B, 11C, and 11D. Coagulation chemistry refers to the end effect produced by the integrated combination of one or more variables, as described below. Coagulant chemical species can include additives variously referred to as flocculants, flocculent aids, and filter aids. A coagulation-chemistry regime for a given application at a site may involve variation of the following elements:

(i) One or more classes of chemical species such as oxidants for Mn/Fe removal, pH adjustment chemicals which can be a 'master variable' that offers significant benefit/$ improvements, hydrolyzing metal salts (such as aluminum sulfate or chloride, ferric sulfate and/or numerous polymerized derivatives), and/or organic polymers of which there are 10's to 100's of species, or combinations.

(ii) Sequence and delay time between additions.

(iii) Mode and details of additive dispersion.

(iv) Concentration of each individual coagulant chemical species.

The optimum combination of coagulant species 11A, 11B, 11C, and 11D may vary with location, raw water quality, treatment quality goals, plant separation processing equipment, and quite importantly may vary with time for a given situation as the input stream of raw water varies in quality. Hence, one needs and instrument downstream of these coagulant addition points to identify whether the correct chemical species and quantities of these species are being added to optimize and control the process. The present invention provides a practical, real-time metric-measuring system and process for monitoring and controlling coagulation-flocculation processing progress.

Overlaying the above is the added complication that there are three distinct domains of optimization: local, global and universe. "Local" refers to the optimum in floc formation for variation of one coagulant species (all other variables held constant). For example, a 'local' optimum would be defined by the data pair corresponding to the maximum value for the metric variable feedback response and the coagulant dosage for a given initial pH in a titration curve traversing a 3-D domain. "Global" refers to the highest "peak" in the entire 3-D domain for example, for variation of dosage (of either metal or polymer) vs. pH domain (at a fixed condition of all other variables). Universe refers to the consideration of all possible combinations of viable coagulant species for a given site and the maxim response of all tested coagulant-species combinations.

The present invention can be used in a variety of water treatment environments, which typically have some or all of the elements show in FIG. 1. Water treatment is a broad field, and there are many water treatment processes and facilities that can benefit from the present invention.

(i) In 1990, a prevailing ideology in leadership of the drinking-water industry was that [strictly] physical processing (membranes, adsorption, oxidation) over chemical-physical processing (coagulation-flocculation, granular-media filtration) was the technology future of the water industry. Coagulation-flocculation was strictly passe. Thus, membranes would obviate the need to waste further resources to quantify and automate the troublesome never-ending problem of adjusting coagulation chemistry in response to raw water quality changes.

(ii) Currently, the prevailing evidence points to the harsh reality that the future of the industry is with a mix of chemical-physical and physical processing. Underlying this transformation of ideology has been the inevitable reality, slowly but inexorable surfacing, that coagulation-flocculation trumps the severe penalties (a threefold effect arising from the increase of first costs, operating costs, and membrane-replacement costs, combined with reduced throughput i.e., reduced benefit/cost) that colloids inflict upon [strictly] physical exclusion-adsorption technologies. Would the existence of appropriate real-time metrics and automation of coagulation-flocculation prior to 1990 have avoided this expensive detour?

(iii) In some cases coagulation-filtration plant performance can be increased between 10-fold to 10,000-fold with through use of the methods and system described in the present disclosure, including usage in optimized coagulation-filtration plants capable of near 5.5-log removal of Giardia and Cryptosporidium versus a 1.5-log removal of Giardia or Cryptosporidium which was the mean value obtained in a nationwide survey of US drinking water plants.

In one embodiment, the present invention can be used in conjunction with turbidity measurement, a common metric of coagulation-flocculation-filtration performance for drinking water. Turbidity is an optical property involving light scattered from particles and is typically measured at the end of the process such as for the treated effluent illustrated at 6 in FIG. 1. The beneficial features of turbidity are that it is:

(a) Automatable, reliable, cost effective instruments used on every individual filter.

(b) Sensitive for retrospectively judging removal success when diligently calibrated and maintained but only following effective coagulation-flocculation.

(c) Quite sensitive to upstream events—but becomes useful for relating cause-effect only following retrospective review to isolate the significant interferences from hydraulic 'noise' and is placed in the context of each filter cycle (following backwash but before breakthrough).

(d) A suitable regulatory compliance tool.

In one embodiment, the present invention complements turbidity measurement by providing:
 (a) Data upstream and earlier than where turbidity can be measured.
 (b) Real time data that characterizes the intelligence laden flocculation dynamics of pretreatment progress.
 (c) A direct measurement of particles prior to the removal process rather than a measurement of particles not removed.
 (d) A more accurate measure of the health risk of the water treatment process water being treated.

In one embodiment of the present invention, the instrument shown at 100 in FIG. 1:
 (i) Measures a surrogate of pollutant-concentration removal success.
 (ii) Works in water treatment facilities that remove pollutants generally representing numerous broad pollutant categories including 100's of genera and species of infections organisms, carcinogens, potentially formed in processing, other health compromising species such as arsenic, mineral mater, stimulants of microorganism growth ($PO_4^{-2}$), FOG (fats, oils and grease), and fibrous material (e.g. asbestos); a significant challenge indeed.
 (iii) Provides real-time feedback of pollutant-removal progress.
 (iv) Can be deployed throughout the entire processing system, including real-time feedback, in situ process analysis, and for use in empirically based reconnaissance testing and mapping of removal in response to operationally controllable variables (coagulation chemistry and mixing).
 (v) Can be calibrated to a known standard.
 (vi) Can be correlated to turbidity—the existing de facto surrogate drinking water filtration standard.
 (vii) Can be used to measure water quantity (net throughput or production volume) as well as removal quality success.
 (viii) Can provide a means to balance among opposing needs and outcomes such as:
  (a) Using empirical based exploratory changes of processing control variables, coagulant dosing, and floc mixing.
  (b) Using the full process to maintain floc-mixing similitude.
 Which can prevent undesirable outcomes such as:
  (a) Increased risk to effluent quality by exploring change of operation-control variables because of using the full process for 'testing'.
  (b) Low similitude level, and increased risk to quality of mapped response by using side-stream simulation exploratory change for flocculation-response mapping.

Further referring to FIG. 1 a suspended particle characterization system 100 is deployed in a clarification 4 unit of a water treatment processing system. The water treatment processing system depicted employs coagulation 2 and flocculation 3 processing units of raw water 1 as pretreatment for the formation of floc particles in preparation for the physical separation of a wide variety of pollutant species piggybacked upon suspended floc particles. Said particles are separated from water by downstream removal processes of clarification 4 followed by filtration 5 of the floc/pollutant suspended particles. In this embodiment, the instrument quantifies the physical characteristics of floc particles entering the clarifier. The physical floc characteristics, manipulated by the upstream processing, collectively represent an optimal control variable that reflect and predict the effects and success of pretreatment for downstream physical separation of floc-pollutant particles. The prime objective of such water purification systems is the removal of pollutant species piggybacked upon floc, which is affected by floc physical characteristics. Because the system 100 quantifies floc physical characteristics, it is pivotal to monitoring and control of pollutant removal. Feedback from system 100 can aid facility operators in performing optimization of the two main control variables, coagulant chemical dosing by a coagulant dosage mechanism 12, and flocculation mixing by a mixing means 15, of a pretreatment processing mechanism.

Processing mechanisms other than clarification 4 and filtration 5 as depicted in FIG. 1, may be employed following coagulation 2 flocculation 3 pretreatment processing. Options may include flotation, various processes based upon gravity, centrifugation, magnetism, or may not employ any intermediate process preceding the final pollutant-water separation process. The separation process may include adsorptive and/or exclusion principles for floc collection including screens, membranes, fabrics, fibers, composites, and granular-media filters. Examples of water processing facilities include municipal drinking water treatment, industrial process water treatment, industrial process wastewater treatment, municipal wastewater treatment, membrane pretreatment (including desalination), recycled water treatment, and advanced wastewater treatment, as well as sludge dewatering, and papermaking or anything similar that can be understood by someone skilled in the art. These processing facilities typically treat thousands if not millions of gallons of water per day for a useful purpose.

Figure 3A:
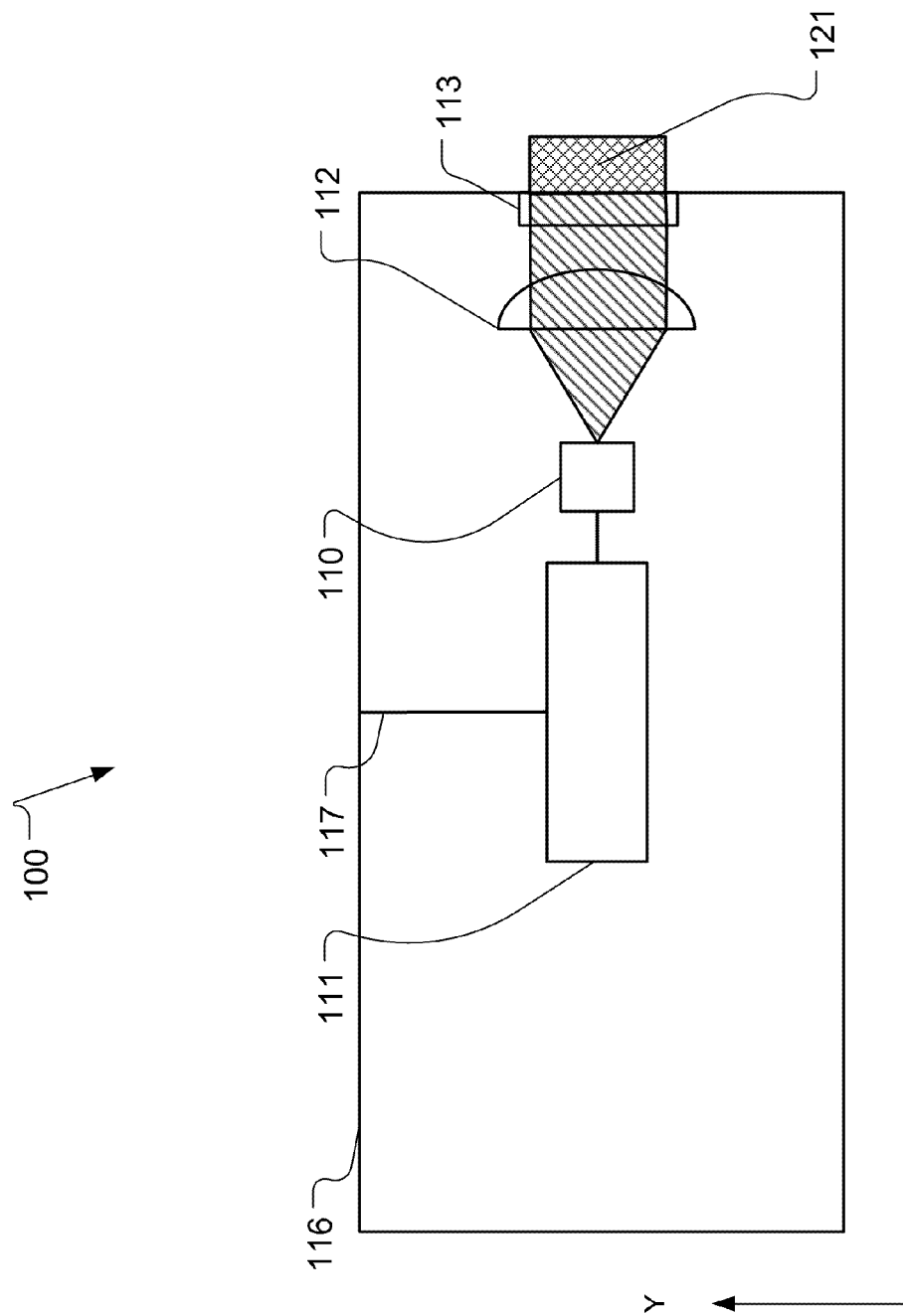
FIGS. 3A-C are schematic views of a preferred embodiment of the suspended particle characterization systems used in FIG. 1.
Figure 3B:
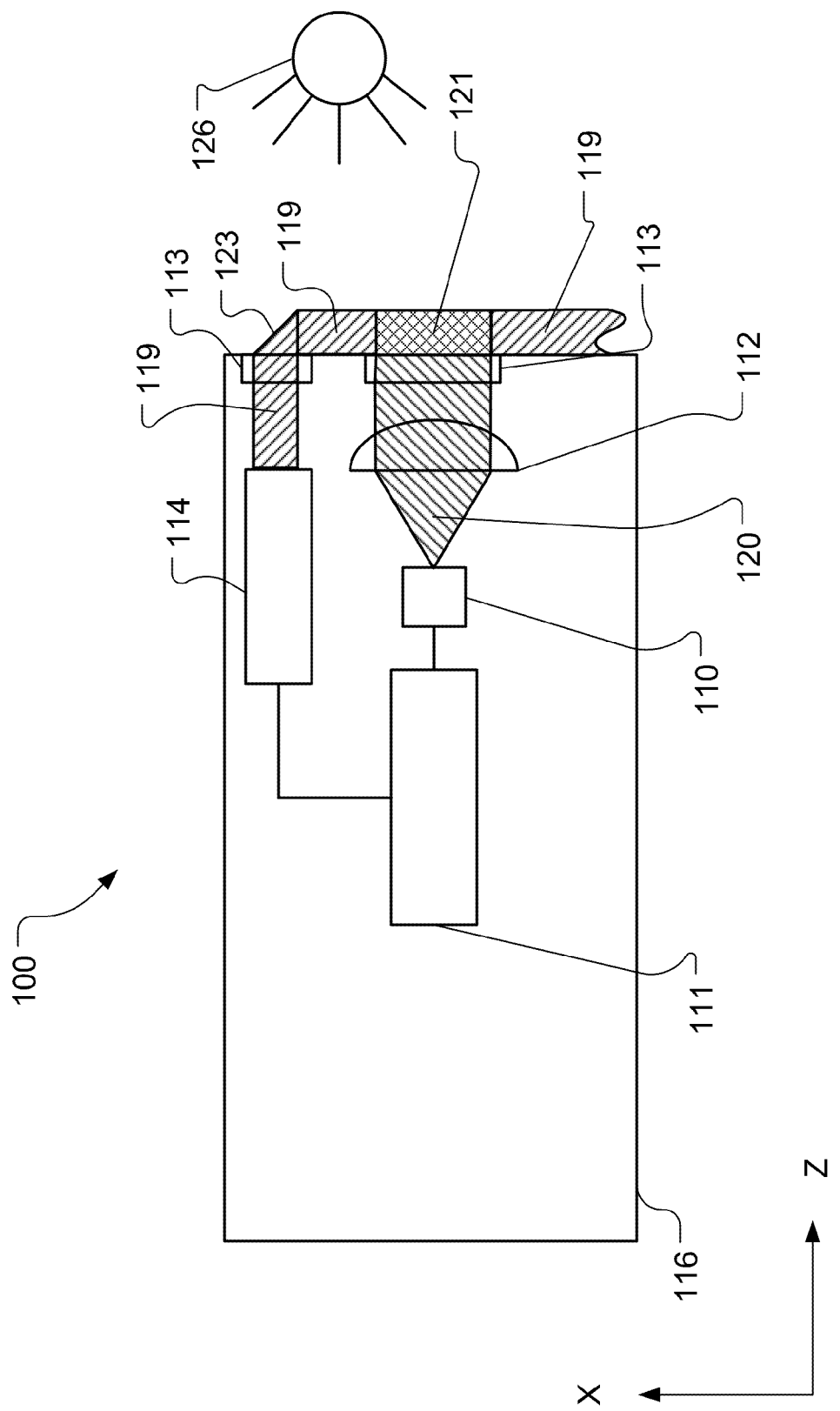
Figure 3C:
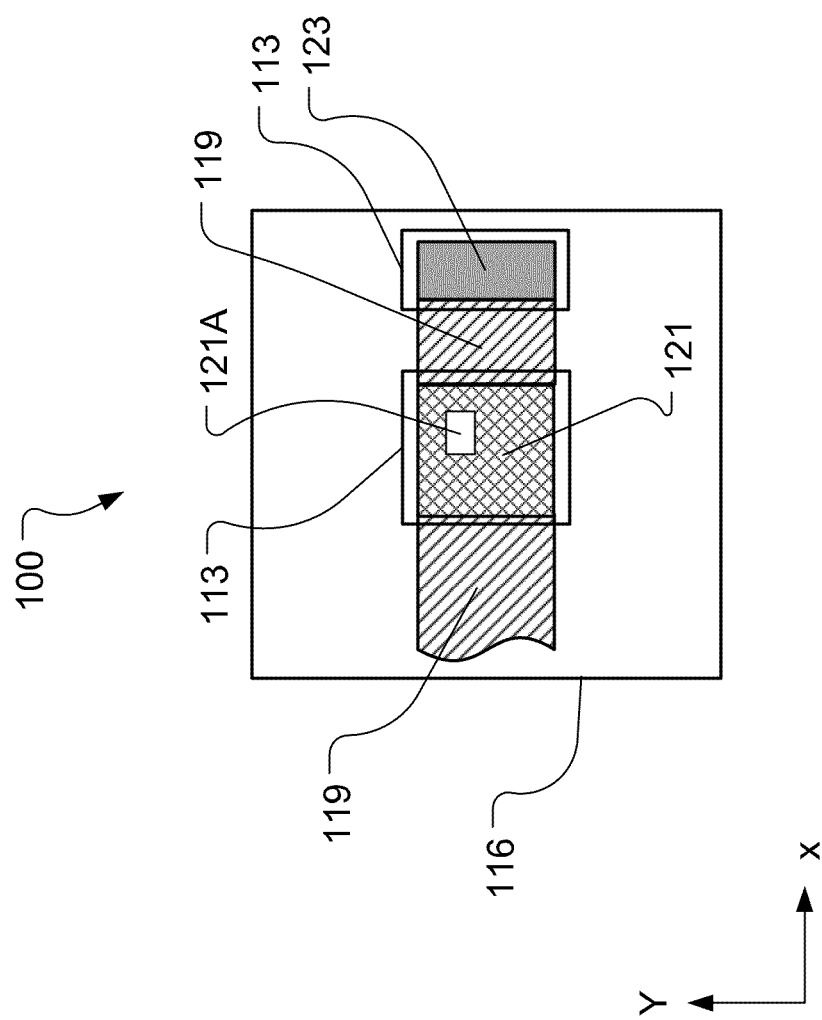

The system 100 construction details are best seen in reference to FIGS. 3A, 3B, & 3C.

The system 100 consists of a housing 116 incorporating an optical window 113 for transmitting floc sample images to an electro-optical image sensor 110 for detection and capture of floc-particle characteristics. Alternatively, optical window 113 may consist of an optical waveguide for transmitting floc sample images to the remotely located image sensor 110. The system 100 should be constructed such that its volume is less than 20 cubic inches, less than 50 cubic inches, less than 100 cubic inches, less than 200 cubic inches, or less than 500 cubic inches. There is an inherent benefit for the system 100 being small. Larger systems may be required to function in alternative environments or locations.

An optical element 112 consisting of a single or group of optical components, transmits the image captured from a sample volume 121 to the image sensor 110. The electro-optical image sensor 110 should be constructed to have more than 500,000, more than 1 million, more than 2 million, more than 3 million, more than 4 million pixels of resolution. The system 100 can output color or grayscale data, with a minimum of one bit pixel data and maximum of 32 bit pixel data. The optics 112 can be constructed to include adaptive features from a group including elements of zoom lens or lenses, automatic or variable focus, automatic, or variable aperture, and adjustable depth of field. Because the computing engine 111 processing load is dependent on the number of particles present in a given image, there is a tradeoff between the pixel count of an image and system performance. In order to optimize the imaging process for a given situation, the adaptive features of the optics 112 can be used to adapt to samples with large-particle/small-count and to samples with small-particles/large-count. Use of either adaptive or fixed features provides the system with the ability to analyze particles down to a minimum particle diameter of 1 micron, 5 microns, and up to at least 10 mm in maximum particle diameter. To accurately detect a particle the apparent image of the particle should encompass at least four pixels of the image sensor. A magnification or enlargement factor of the optics 112 must be known so that actual object size can be derived from an image of an object using known values for the distance from the image sensor 110 to object, and the magnification factor of the optics 112. This adaptation can also occur through software methods, by sampling only a portion of the image sensor as illustrated in FIG. 3C by a region of interest 121A.

Each image is analyzed in a computing engine 111, as elaborated upon in the detailed descriptions of FIGS. 4, 5, 6, and 11. The sample volume 121 is determined by the intersection of an optical view volume 120 and an illumination volume 119 as illustrated in FIG. 3B (horizontal cross section). FIG. 3B depicts that the illumination volume 119 originates from an illumination assembly 114 in a collimated form. Alternative embodiments of illumination means 114 may include but are not limited to non-collimated, forward, dark field, low-angle forward scattered, or other means understandable by someone skilled in the art. The illumination assembly 114 is oriented with its optical axis parallel to the optical view volume 120 axis (see FIG. 3B) and is horizontally displaced (see FIG. 3C). The emitted illumination volume 119, whose initial axis is parallel to said view volume 120 axis, is redirected by an optical prism 123 (or optionally a mirror, light pipe or other light bending means) such that its redirected axis is exterior to the optical window 113 and passes through the axis of the optical view volume 120. The illumination assembly 114 can be capable of modulating the supplied light intensity or incident angle relative to the image sensor to adapt to particle reflectivity, ambient light level, image acquisition time, particle concentration, particle size, or a combination of these or similar variations in the sample. The modulation of supplied light intensity can be implemented through the use impedance-varying means, current-varying means, or pulse-width modulation. The modulation of supplied light intensity can be automatically controlled by the computing engine 111 or manually controlled by a user.

In order to capture image data that accurately represents suspended particles it is desirable to have a short image acquisition time. The image acquisition element, consisting of a combination of the image sensor 110, the optics 112, and the illumination assembly 114, can be capable of capturing an image in an elapsed time shorter than 10 ms, shorter than 100 ms, shorter than 1000 ms, shorter then 10000 ms. Floc particle movement occurs continuously within the sample volume 121 due to the floc particle settling, in this case of the preferred embodiment, in the clarification 4 unit (FIG. 1). Alternatively, when deployed in turbulent mixed processing units or sample side-stream units, such as in this or an alternative embodiment, fluid and particle motion adjacent to the optical window 113 is continuous and chaotic. Turbulent dynamic environments result in continuous renewal and random motion of the floc particles in the sample volume 121.

The system 100 may include an optical surface cleaning element, such as the optical surface wash pump 126 (FIGS. 3A and 3B). The optical window 113 and the optical prism or mirror face 123 are examples of optical surfaces. The washer 126 can incorporate at least one nozzle or jet oriented at and placed near the optical surfaces so a flow of fluid or gas can be activated to remove objects or fouling on the optical surfaces at an interval determined by the system 100 or defined by a user. This cleaning function can be accomplished by alternative means including but not limited to wiper blades, brushes, ultra-sonic mechanisms, thermal mechanisms, surface coatings, or combinations. Finally, the system 100 is connected with a plant process network, communications, and control system 7 by a communications and power cable 117.

The system 100 employs three critical design features best understood in reference to FIGS. 3A, 3B, and 3C.

First, the system 100 has no protruding physical features vertically above or below the sample volume 121 to impair flow or otherwise disrupt floc characteristics (see FIG. 3C). This enables floc particles to pass unobstructed vertically through the sample volume 121 under the influence of gravity when the system 100 is located in environments isolated from fluid-motion forces. By capturing sequential images of these settling floc particles, the system 100 can accurately calculate gravitational settling velocity. The significance and methods of use of such a measurement are discussed in the detailed description of FIG. 9. Such an unhindered, error free measurement would be rendered impossible by the required physical elements, namely flow baffle plates, of the prior art (see FIG. 2B). There is also an absence of flow disruptive physical features of the prior art, such as flow baffle plates, employed for the specific purpose of restricting floc-sample flow velocity into the sample volume 121. This physical design difference from the prior art is necessary for ensuring the elimination of fluid-shear-induced breakup of floc structures and the resultant errors in floc characteristic measurement.

A second critical design feature is the ability to define a sample volume in which suspended particle characteristics can be measured. A defined sample volume is desirable and necessary to express floc-particle volume, number, and mass in units of concentration. In turn, the latter three variables are fundamental to normalizing or providing a baseline across instrument variation. Additionally, an ideal metric must reflect pollutant-floc reduction in concentration. In one embodiment, the sample volume can be defined based on three orthogonal vectors. Each vector can be used to define a pair of planes parallel to each other and normal to the vector. The six planes defined in this way enclose the sample volume 121. The position of the pair of planes normal to the view volume 120 is specified by the width of the illumination volume 119 as depicted in the horizontal cross-section of FIG. 3B. The position of the two remaining pairs of planes can be modified by a user or automatically by the computing engine 111 to define a region of interest 121A (see FIG. 3C) within the image plane specified during image acquisition. The region of interest 121A is a portion of the total image area 121. A further discussion of its uses and how it can be specified is found in the detailed description of FIG. 4. For the preferred embodiment the sample volume defining means should produce a sample volume 121 of not more than 100 cc, not more than 20 cc, not more than 10 cc, not more than 5 cc. Smaller sample volumes can be used when there are more numerous, smaller particles, conversely a larger area could be employed for large, sparsely numerous particles in order to ensure that a statistically acceptable sample volume is analyzed. The computing engine 111 processing load is dependent on the number of particles present in a given image. In order to achieve good system performance for both image sample rate and particle count, the sample volume 121 and region of interest 121A must be large enough to encompass many particles, yet small enough that the system performance does not diminish. The adaptive features of the optics 113 and image sensor 110 parameters can be controlled by the computing engine 111 to optimize the image acquisition element to provide the balance between sample rate and particle count. As the art of image sensors 110 and computing engine 111 technologies improve, those advancements can be used to facilitate larger particle counts and sample volumes without diminished system performance. Testing of the system 100 used in design of the preferred embodiment, employed a sample volume in the 2 cc to 3 cc range. Alternative embodiments of establishing sample volume defining means are discussed in connection with FIGS. 7A and 7B below.

The third critical design feature is a communication element. A versatile, readily adaptable communication element is of critical importance for application of system 100 to the large number of facilities comprising the existing water purification infrastructure; that possesses a range of hardware and protocols in their control networks. The communication element incorporated in system 100 is capable of transmitting and receiving data through analog and digital electrical signals. The communication element can also transmit and receive data over wireless communication protocols. The communication element can communicate with the plant process network, communications, and control system 7 by the cable 117. Instrument outputs may be transmitted over analog means, such as a 4 mA-20 mA, or 0-5 volt signal used in plant supervisory control and data acquisition (SCADA) systems or over digital serial protocols such as TCP/IP, USB, MODBUS, FIELDBUS, CANBUS, PROFINET, or any similar protocol capable of being understood by someone skilled in the art. When an appropriate communication signal is used, particle characterization system outputs can be conveyed through histograms, graphical means or numerically. The communication element can also be capable of communicating control signals for process related systems. These target systems may include pumps (used for chemical injection, sample acquisition and collection, and hydraulic flocculator), motors (used for mixing), and valves (used for process flow control, sample selection means, flow direction, or fluid injection) or similar hardware understandable by someone skilled in the art. The communication element should also provide a means for allowing multiple system 100 units to be employed in a single facility and to communicate results between each other.

The system 100 can be manufactured and deployed as a submersible waterproof in situ probe directly in the process when appropriate connectors and cabling is provided to the surface for the communications and power cable 117. Alternatively, the system 100 can be manufactured for out of water use where lower water resistance tolerances prevail. For such an alternative embodiment, waterproofing is required only for the portion of the system 100 directly in contact with a coagulated liquid 13.

Operation of FIGS. 1 and 3 further define the preferred embodiment of the system 100, its capabilities, application, and use.

The instrument 100 can operate in either of two modes: continuous-flow sampling and batch sampling. Continuous-flow sampling is where the fluid sample is being continuously refreshed by an upstream fluid. Analysis in continuous-flow mode allows the system 100 to repeatedly measure samples at the same point in the treatment process and therefore at the same point in floc-particle maturation or growth. By comparing the results of one sample to a later one collected after a change to the upstream process has occurred, the system 100 can show the change's effect on floc-particle maturation.

Batch sampling is where the fluid sample collected and isolated from the process and therefore has no further mass exchange. The isolated fluid sample should have a volume of less than 1/100, less than 1/1,000, less than 1/10,000, less then 1/1,000,000 times the volume of it source. Its lower limit is equal to the sample volume 121. Its upper limit is equal to the volume of the vessel the system 100 is monitoring. The fluid sample remains isolated until all desired measurements are completed or an operator releases the fluid. This can occur over an elapsed time of a few seconds to multiple hours depending on what information is desired. The fluid sample is then discarded either to waste or back into the process. Batch sampling provides the ability to capture floc-particle maturation and aggregation of the discrete sample over time and/or floc gravitational settling.

The system 100 senses floc particle characteristics. Seven such floc particle characteristics are: volume concentration $V_c$, number concentration $N_c$, gravitational settling velocity $v_g$, mass density $\rho$, mass concentration $M_c$, computed particle volume V, and synthetic particle diameter $D_s$.

Volume concentration, $V_c$ is defined as the sum total volume of all particles in a fluid sample divided by the fluid sample volume. It may have the units of cc/l, where cc is cubic centimeters, and l is in liters, or another suitable unit of volume per unit volume.

Number concentration, $N_c$, is defined as the total number of particles in the fluid sample divided by the fluid sample volume. It may be reported in the units of 1/l or another suitable unit of number per unit volume.

Gravitational settling velocity, $v_g$ is defined as the velocity of a particle or the average of all particles in a fluid sample, when the particle(s) are being acted upon predominantly by the force of gravity. The direction of the vector must be in a predominantly downward or settling direction. It may be reported in the units of mm/min or another suitable unit of speed.

Mass density, $\rho$ is defined as the mass per unit volume of a particle or the average of all particles in the fluid sample. It may be reported in mg/cc, where mg is milligrams, or another suitable unit of mass per unit volume. Mass density may alternatively be measured directly with a device such as a scale or balance, or it may be derived from other variables.

Mass concentration, $M_c$ is defined as the total mass of all particles in a fluid sample per unit volume. It may be reported in g/l where g is grams, or another suitable unit of mass per unit volume.

Computed particle volume, V is defined as the volume of a particle or the average of all particles in a fluid sample. It may be reported in the units of cc or another suitable unit of volume.

Synthetic particle diameter, $D_s$ is the defined diameter of a sphere with an equivalent volume to that of a particle or the average of all particles in a fluid sample. It may be reported in microns or another suitable unit of length.

Other potentially measurable or derived floc particle characteristics may include shape factor, reflectivity, porosity, shear resistance, strength, ductility, buoyancy, stickiness, and uniformity.

The reported variable(s) may be for individual particles or they may be expressed as average value(s) for all particles in a fluid sample or distributions. The particular variable set measured depends upon the environmental conditions where the system is located or upon user requirements. The three possible environments and respective variable sets are:

(i) Mixed—$V_c$, $N_c$, $D_s$
(ii) Settling—$V_c$, $N_c$, $D_s$, $v_g$, $\rho$, and $M_c$
(iii) Transitional—$V_c$, $N_c$, $D_s$.

Mixed environments prevail in situations where fluid is flowing, such as in a conduit, where air bubbles exist, or when mechanical mixing is imposed, such as a flocculation reactor 14 configured as a full-flow continuous process (FIG. 1). A mixed environment also occurs in a batch reaction mechanism where a discrete volume of a coagulated liquid 13 is continuously mixed over a finite period (see FIG. 8A, 8C, 8D, 8F, or 8H). Transitional environments occur in situations where the mixing inducing forces have stopped but where non-gravitational forces are still exerted on the floc particle movement. Settling environments result after these, additional forces have dissipated leaving the force of gravity as the predominant force exerted on the floc particles. These various environments exist at different points in the process, in isolated samples, and in coagulate liquids contained in the alternative embodiments discussed in connection with FIG. 8.

The system 100 can be mounted at or in any of the environments (see FIG. 1) in order to sense a set of desired variables. If an operator wished to know only $V_c$, $N_c$, or $D_s$ the particle characterization system could be placed in any mixed or transitional environment location such as at a coagulation influent to flocculation 16A or downstream of a coagulant plug-flow dispersion unit 10PF site 13A-13D. If the operator wished to know $v_g$, $\rho$, or $M_c$, the system 100 would have to be placed in a settling environment such as in the clarifier 4 as it is shown in FIG. 1, or in a flocculation mixing vessel 14 or conduit 128 after the mixing means 15 or flow in a conduit 128 has stopped and the fluid has completed the transitional environment stage to a settling environment stage.

Multiple systems 100 may be used simultaneously in order to provide additional user benefits. For example, systems 100 can be located at any or all of the multiple points along the pollutant separation processing train (see FIG. 1). These locations include, but are not limited to:

sampling the raw water 1A, coagulation 2 processing following mixing with the raw water 1 in a coagulant dispersion plug-flow unit 10PG, or other type dispersion unit, and subsequently sampled at any one or all locations including but not limited to:
  full-process coagulated effluent stream species A sampling point 13A,
  full-process coagulated effluent stream species B sampling point 13B,
  full-process coagulated effluent stream species C sampling point 13C, and
  full-process coagulated effluent stream species D sampling point 13D respectively,
within or following flocculation 3 processing at any or all location including, but not limited to;
  near an entrance to floc processing 16A,
  near an exit of the initial floc reactor 16B,
  near an exit of an intermediate floc reactor 16C,
  near an exit of the terminal floc reactor 16D or
  in a effluent stream of floc reactor 17A
within in or surrounding clarification 4 processing including but not limited to;
  near an influent stream to clarifier 17A,
  within the clarifier (see FIG. 1)
  in a effluent stream from the clarifier 17B, and
  in a clarifier underflow 8
within or surrounding filtration processing including but not limited to;
  in an influent stream to the filter 17B,
  in an effluent stream from the filter 6 and
  in a flow stream from filter backwash 9,
as well as other locations along side-stream flows diverted from any or all location including but not limited to;
  full-process coagulated effluent stream species A sampling point 13A,
  full-process coagulated effluent stream species B sampling point 13B,
  full-process coagulated effluent stream species C sampling point 13C,
  full-process coagulated effluent stream species D sampling point 13D or
  any or all full-flow continuous process observation points 16A-16C or
  any or all sensor observation points 17A-17E, 6, 8, or 9.

Sampling and analysis of these and other location sets produce critical new information for facility operation and control including the pretreatment for floc-pollutant formation success because of the level of addition of each individual coagulant-chemical species; new benefits deriving from this include the ability to:

(i) Systematically monitor the floc formation effectiveness of each individual coagulant species in an additive fashion thereby achieving the elusive goal of full-processing similitude of coagulation chemical manipulation;

(ii) Divert sample streams of each coagulant additive for reconnaissance floc-response mapping off-line of variation of coagulation chemistry and floc mixing at no risk to full-process effluent quality;

(iii) Mass balances reflecting floc-pollutant formation and removal effectiveness;

(iv) Ability to oversee and orchestrate the floc mixing mechanism to tailor individual mixers to contribute to improved removal processing performance;

(v) A range of side-stream empirical testing for mapping floc response to control variable manipulation, for example.

The system 100 can have preprogrammed limits and provide alarm signals if particle characteristics exceed a threshold. Such a warning can be triggered when a particle characteristic rate of change exceeds a predefined rate. Thresholds can be defined by a user or established by the computing engine 111 based on historical data and pattern recognition algorithms. Threshold values could be established based on values of various particle concentration variables, size, apparent particle speed, particle density, or any other measured or derived particle property.

Figure 2A:
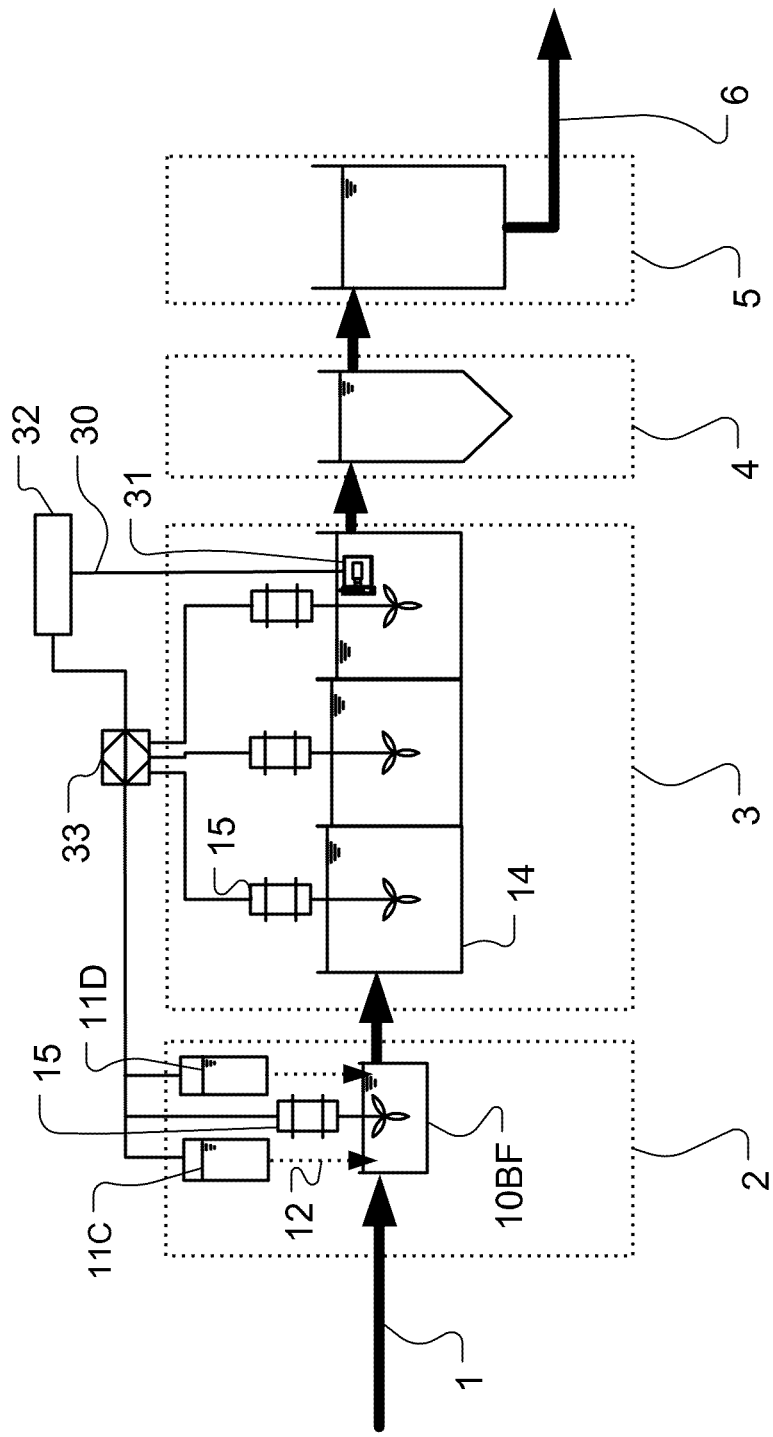

FIGS. 2A and 2B depicts an example of the construction and design of a prior art system.

FIG. 2A depicts water treatment system representing the prior art to the system represented in FIG. 1. The related prior art—U.S. Pat. Nos. 4,654,139 and 4,783,269—describes, a floc image pickup means 31, (depicted in a vertical cross section) for an in situ monitor of floc particles located near the flocculation process exit in water treatment process where it was employed for operational process control. The floc image pickup means 31 was connected by communications and power cable 30 to an image process system 32 that in turn communicated with a controller 33. In U.S. Pat. No. 4,654,139 the floc image pickup means 31 was used for control of the rotational speed of one or more mixer-motors 15 that induce turbulent fluid motion and floc-floc-particle collisions that result in aggregation or suspended floc particle size increase. In U.S. Pat. No. 4,783,269 the floc image pickup means 31 was, instead, employed for control of one or more coagulant chemical species 11C and 11D with the coagulant dosage mechanism 12 with the floc image pickup means 31 also located near the flocculation process exit. Coagulant dispersion was accomplished by employing a back-mix dispersion unit 10BF involving a motor driven variant of the mixing means 15.

FIG. 2B is a diagram of the construction of the floc image pickup means 31. The floc image pickup means 31 included a floc analysis zone 41 that was contained on four or more sides with offset floc sample flow-limiting openings around a series of baffle plates 36 and a back screen 37. The remaining side was composed of an optical window 40 and a watertight container 35 wall. An industrial TV-camera system 34 captured images transmitted through the optical window 40 from a floc analysis zone 41. The floc analysis zone 41 was composed of the intersection of an illumination-light source 38 and illumination volume 42 and the optical sample volume 39. The image information from the TV-camera system 34 was transmitted electronically to an image processing system 32 (see FIG. 2A) via communication and power cable 30.

Local, random, transient high velocity turbulent eddies may occur in large-scale floc chambers 14 and floc velocities must be first reduced before entering the floc analysis zone 41 in order for this system to operate. The flow restrictions provided a reduction of ambient flow velocity from that of the turbulently mixed process floc chamber 14 into the floc analysis zone 41. This design feature reduced floc particle velocities to a speed low enough for successful image acquisition. Without the flow restriction means, particle movement during the shutter-open period, would have appeared as streaks, thereby distorting the apparent 2-D-floc-image area and would have resulted in errors of increased apparent floc size. Such flow restrictions were employed to overcome this apparent streaking. However, the flow restrictions created an unanticipated effect, the opportunity for floc particle shear, which can result in the breakup and consequent size reduction of floc particles. The probability of such high-shear/size-reduction is elevated as effectively, a few selected members of a moving floc 'heard' are abruptly directed and confined, in order to reduce their velocity during observation. The prior art sensor would have reported incorrect, distorted measurements with no acknowledgement or means of compensation for these designs, error-inducing restrictions.

The differences in FIG. 1 and FIG. 2 systems operation further highlight the distinguishing features and limitations of the prior art.

The operation of system 100 as depicted in FIGS. 1 and 3A-3C is similar to that of the prior art (FIG. 2B) in some respects but differs significantly in others. Both systems remain in place at a fixed location in a constantly flowing environment. Both systems continually analyze floc particle characteristics formed during upstream processing, yet numerous differences exist. First, system 100 utilizes an adaptive volume calculation method selection means to ensure that the most accurate volume approximation calculation is always used for each particle. Second, system 100 can be mounted in multiple environments and virtually any location along the process treatment train whereas the prior systems were limited in placements and therefore limited in their capabilities. Third, the prior art systems had no means of determining mass density or mass concentration. Finally, the system 100 logs and communicates its results to a variety of network types, either new or preexisting in a water-purification-plant environment. In contrast, the prior art devices communicated their results directly to its own slave controller 33 for process manipulation.

Figure 4:
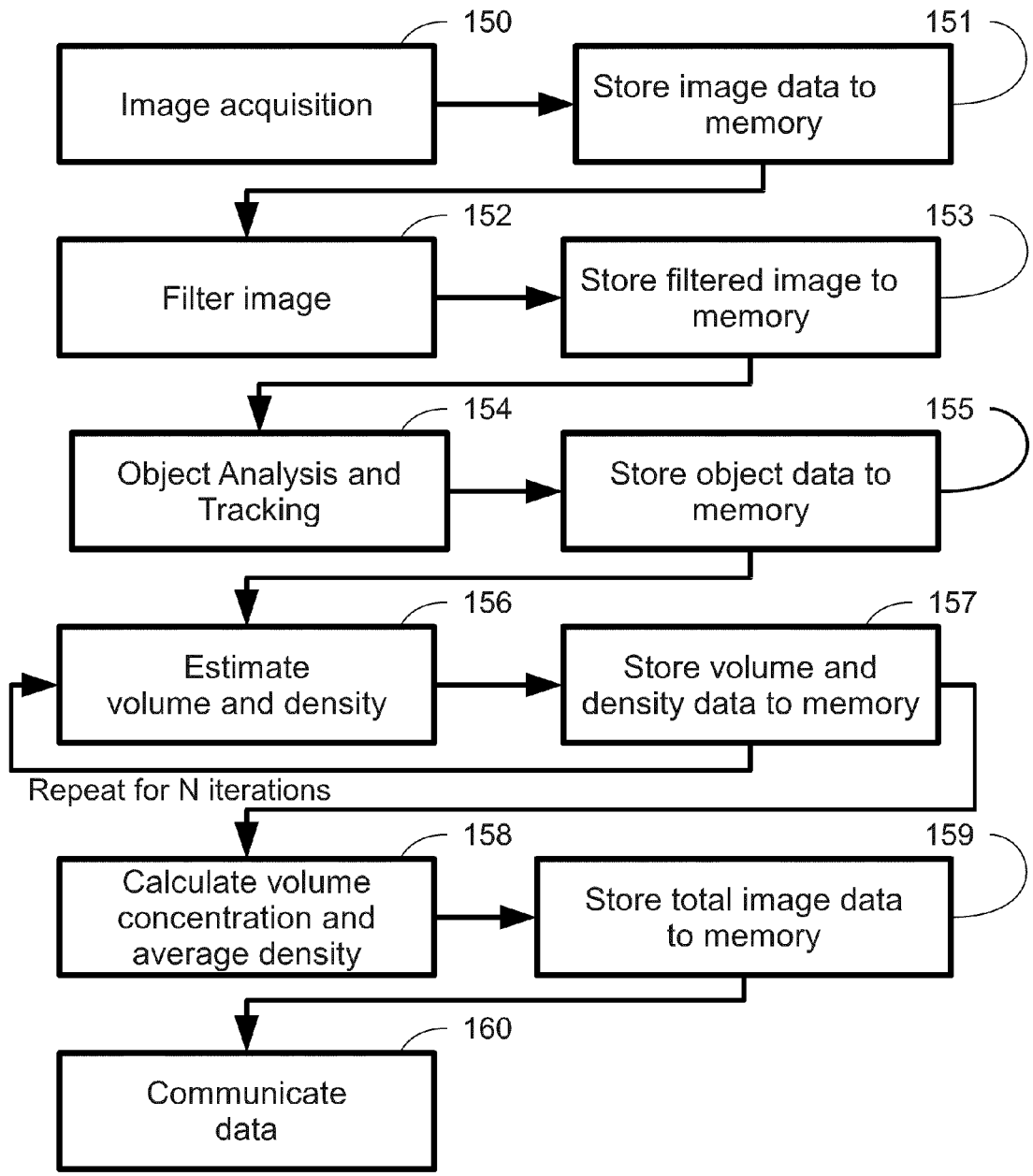
FIGS. 4 and 5 are functional block diagrams of the present invention.

FIG. 4 depicts an example of a logic flow used in the system 100 and is described in detail below.

The processing reflected in FIG. 4 follows the logic flow through the detailed steps by which the system 100 performs transformation of acquired floc image information from the image sensor 110 into floc particle physical characteristic values—$V_c$, $N_c$, $D_s$, $v_g$, $\rho$, and $M_c$, by the computing engine 111 for communication to the process network, communications, and control system 7 (see FIG. 1).

Each image-digitized data set is acquired 150, and stored in memory 151. The image acquisition process may sample a visible area equal to or less than the area visible within the optical view volume 120 by observing only the region of interest 121A (see FIG. 3C). The region of interest 121A can be specified by a human operator or an automatic image control means for neglecting image data that does not contribute or introduces error into otherwise useful measurement of floc characteristics. Examples include a view of a portion of the housing 116, or optical aberrations such as solid matter adhering to the optical window 113. A reduced region of interest may also be useful for the measurement of very small objects, when the object count of the sample volume 121 is sufficiently large to induce slow system performance. The stored image data from 151 is filtered 152 through numerical transformations to enhance image quality by procedures focused around object edge data in the image. The transformations include, but are not limited to, level threshold and adjustments of contrast or brightness. Additional transformations such as a sobel filter, for edge enhancement, may be used to highlight the apparent edges of particles in the image. The post-filtered image data is stored to memory 153.

The filtered image data is read from memory and object analysis and tracking procedures 154 are performed on the filtered image data. The system performs operations based upon identifying closed object areas to determine if an object qualifies for further processing. If an object violates predefined threshold value of shape factor or size, or is bisected by the border of the region of interest 121A, it is rejected and not considered for subsequent analysis. Qualifying objects are assigned a number based on position, and a total object count is performed for the entire image. For each object the apparent frontal area (A), perimeter (P), and circularity (O) are calculated. Starting with a second image, a comparison is made with previous images that are held in memory in order to track individual object movement and compute a velocity vector ($W_o$). The data, (object count (N), apparent frontal area (A), perimeter (P), circularity (O), shape factor, object location, ID number, and velocity vector ($W_o$)) is subsequently stored in memory 155.

The system estimates the volume and density 156 of each individual detected object. Object data is read from memory 155. Based upon each object's data, such as area, perimeter, circularity, or shape factor, the step 156 identifies an optimal volume estimation method for each individual object and subsequently estimates volume and density (Note, FIG. 5, discussed below, and the related text expounds upon the individual detailed steps actually involved in executing action 156). Individual object volume ($V_i$) is calculated utilizing the selected method. Additionally, mass density ($\rho$) is calculated for all objects with a velocity vector ($W_o$) that is predominantly in the direction of gravitational settling. The estimation of volume and density 156 is repeated for each identified object in each individual frame and the calculated data (individual object volume ($V_i$), gravitational settling velocity ($v_g$), and individual mass density ($\rho_i$)) is stored in memory 157 at the end of each processing cycle. This cycle continues until all individual detected objects are processed.

Volume concentration and average density are calculated 158 based on the data previously stored to memory 155, 157. All the individual object volume ($V_i$) values are summed together to create a total objects volume value ($\Sigma V_i$). Dividing the total objects volume value by the sample volume 121 ($V_O$), establishes a ratio of floc object volume to sample area volume, or floc volume concentration ($V_c$). A region of interest correction factor ($ROI_c$) can be used to correct for the usage of a reduced region of interest 121A from the sample volume 121. Average mass density ($\rho_A$) is calculated by dividing the summation of all individual mass density ($\rho_i$) values by the total object count (N). The total image data is stored in memory 159 for long-term storage and is communicated 160 via the cable 117 (see FIG. 1) to the plant process network, communications, and control system 7.

$$V_c = \frac{\sum V_i}{V_o} * ROI_c$$

$$\rho_A = \frac{\sum \rho_i}{N}$$

Figure 5:
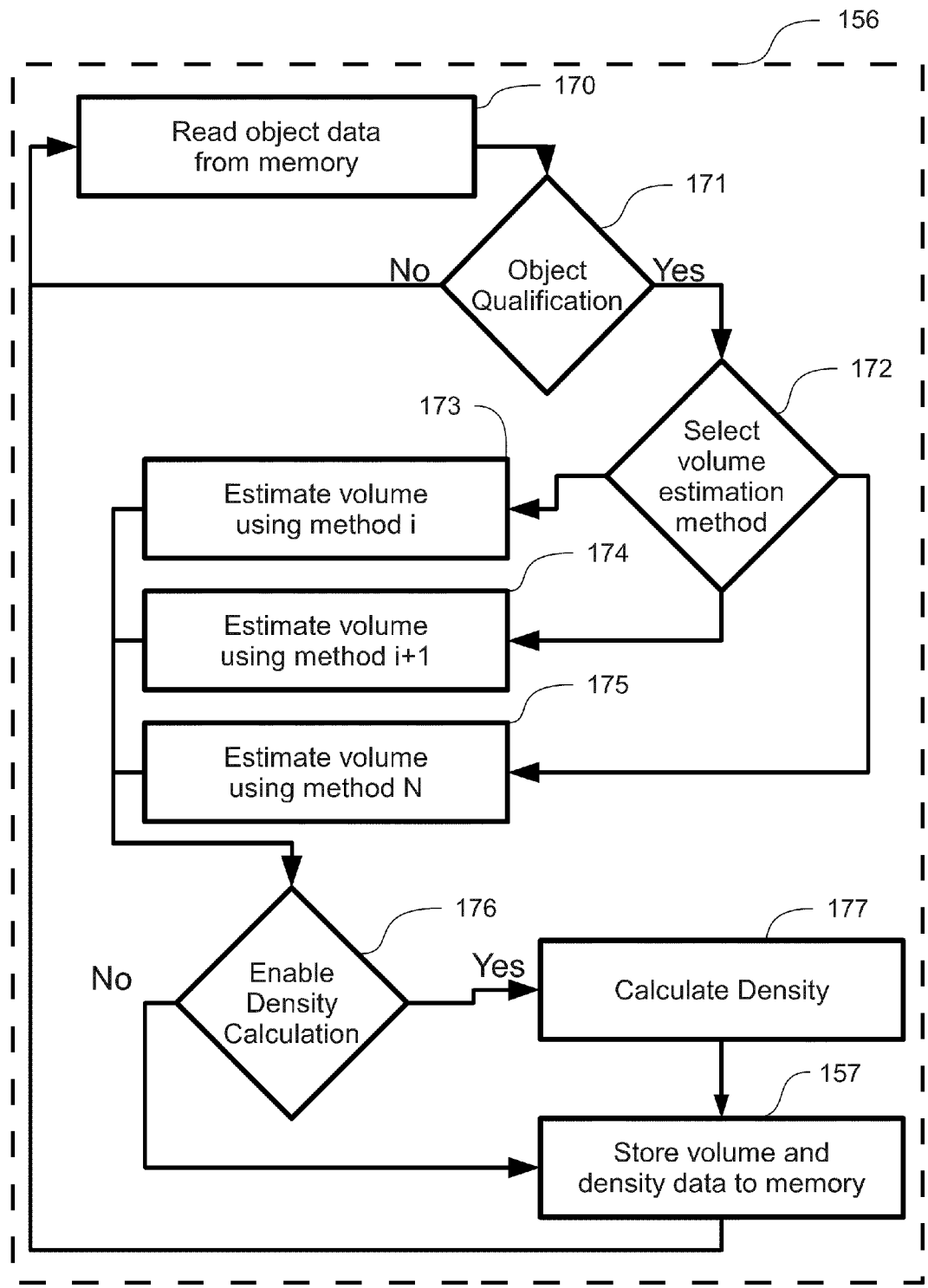

FIG. 5 depicts a logic flow for the specific sequence of actions that comprise the estimation of volume and density 156 and is described below.

The estimation of volume and density 156 computes the individual object volume ($V_i$) and individual mass density ($\rho_i$) values for all objects comprising each individual image processed. As illustrated, this method involves two conditional decision making steps, combined with a repeating loop for processing all qualifying objects from each individual 2-D image. Such a process is needed for two reasons. Firstly, the method of volume concentration used in the prior art exceed deviation from known true volume for all other known methods (as documented below in connection with FIG. 6 detailed discussions). Alternative methods of volume analysis must be used in order to minimize deviation or errors in the analysis of irregularly shaped particles such as floc from 2-D images. Secondly, floc particle density is a highly variable characteristic that must be measured in order to effectively analyze and fully characterize floc for use in coagulation-flocculation control (see FIG. 9).

As depicted in FIG. 5, objects are qualified or rejected for volume estimation by qualifier 171 based on predetermined metrics or adaptive analysis to determine fitness for volume estimation. Numerical criteria for qualification may be based on, but not limited to, circularity (O), apparent frontal area (A), perimeter (P), and shape factor. The object qualification 171 reads the object data from memory 170 to retrieve the data corresponding to the next object in the frame, and then the object data for the qualified object is passed on to be used for the selection of an optimal volume estimation method 172 for processing (continued below). If an object fails to qualify 171, it is not included in any further analysis. Once all objects for a given frame have been analyzed, the volume and density estimation process 156 is complete for a given frame. The image processing then continues with the volume concentration and average density calculation 158 as depicted in FIG. 4.

In reference to FIG. 5, the object data qualified for volume estimation is used to select an optimal volume estimation method 172. The optimal method of volume estimation varies with object shape, necessitating the use of one of a variety of methods to accurately estimate individual object volume ($V_i$). The volume estimation method selection 172 may be based on predefined numerical threshold values, including but not limited to shape, or measures of circularity (O), where (O) is defined as the apparent frontal area to perimeter ratio (A:P), or other parameters based on statistical analysis and pattern recognition algorithms. A variety of volume estimation methods may be considered for the volume estimation method selection 172, as depicted in FIG. 5 by blocks 173, 174 and 175. These methods use data stored in memory to estimate individual object volume ($V_i$). The volume data calculated by one of the volume estimation methods 173, 174 or 175 is stored to memory 157.

Object tracking data previously stored to memory 155 is read by the central processing unit 180 for use in determining if density calculation can be enabled for a given object. The logic for enabling density calculation 176 uses the retrieved object tracking data to determine if an object's movement satisfies predetermined or adaptive, criteria for fitness for density estimation. In a transitional or settling environment the density estimation fitness criteria is based on object motion. Observed motion should demonstrate slow, sinking movement driven dominantly by gravitational forces in order to qualify for density estimation. The system can also identify and ignore objects that are attached to the optical window 113 and are impeding or partially fouling the camera view. The system can identify such problematic objects by tracking their position or persistent offsets in pixel brightness or color over a sequence of images. If historical data indicates that an object is not moving, it can be discounted for analysis and characterization. The computing engine can analyze the discounted object image data to determine if they are translucent or opaque. If the discounted objects are opaque, the pixels comprising the object can be fully discounted from image analysis. If pixels are fully discounted from image analysis the computing engine can apply a correction factor to compensate for the change in sample volume due to reduce image pixel count. If the discounted objects are translucent, the computing engine can apply a compensation factor to the affected pixels to offset the apparent fouling. Objects that are partially within the image frame or region of interest can also be identified and ignored. If the system density calculation enable means 176 detects an image captured in a mixing environment, it rejects the object because settling due to gravitational forces does not occur. If an object is rejected for density calculation, all density related processes are skipped and the volume and density estimation calculation 156 will begin for the next object in the frame. If an object is accepted 176 for density calculation, the object data is passed for density calculation 177.

The density calculation 177 step uses each individual objects' volume ($V_i$) and velocity vector ($W_o$) to solve for the force that a settling object exerts on the fluid medium using the Navier-Stokes equation. Fluid medium density ($\rho_f$) and viscosity ($\mu_f$) are assumed as known values unless otherwise determined. The force of the settling object is assumed approximately equal to the weight of the object at the terminal velocity. Individual mass density ($\rho_i$) is then solved for using the object's weight ($F_{weight}$), individual object volume ($V_i$) and known force of gravity (g), by the following the equations:

$$F_{weight} = V_i \rho_f g + 3\sqrt[3]{6}\, s^{2/3} \mu_f W_o \sqrt[3]{V}$$

$$\rho_i = \frac{F_{weight}}{V_i g}$$

The individual mass density ($\rho_i$) calculated by the density calculation 177 is stored to memory 157. Following completion of the density calculation 177, data are stored to memory 157, and then the entire cycle of volume and density estimation 156 is repeated for the next object until the last identified object in the frame has been processed and stored to memory 157. Next, image processing continues (refer to FIG. 4) to the volume concentration and average density calculation 158.

Figure 6:
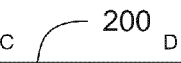
FIG. 6 is an explanatory table useful for explaining different methods of volume estimation.
Figure 6:
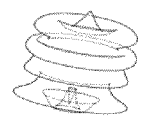
Figure 6:
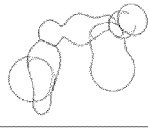
Figure 6:
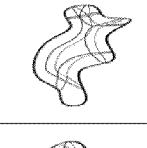
Figure 6:
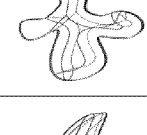
Figure 6:
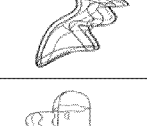
Figure 6:
Figure 6:
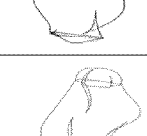
Figure 6:
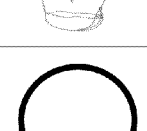

FIG. 6 demonstrates different methods for volume calculation and illustrates their accuracy.

A volume estimation methods table 200 summarizes the average results of calculated volume divided by actual volume. That average, expressed as a percentage, for the five different methods of volume estimation (columns) performed across nine differently shaped sample objects (rows) is calculated such that a value of 100 represents a perfect approximation of each objects known volume. The nine different sample objects were created by a 3-D modeling application allowing the actual object volume to be explicitly known. Images of the sample objects were acquired and analyzed by a process similar to FIG. 4. The numerical results tabulated in FIG. 6 were computed utilizing the five volume estimation methods (heading each column and enumerated below) where each object was rotated along multiple random axes. The volume approximation methods investigated, can be separated into two groups based on the number of geometric properties employed; the groups being methods that use only one property, and methods that use more than one property. Geometric properties are directly observable and include centroid, area, circularity, position, and perimeter. Centroid is the intersection of all strait lines that divide an object into two parts of equal moment and is known as a geometric center, or barycenter. Area is the apparent frontal area of an object as observed by the image sensor 110. It may also represent the apparent area of the object as witnessed by a different point of reference. Circularity is a numerical quantity representing the degree to which an object is compact. Measures of circularity used may include shape factor, circularity ratio, fractal dimension, or sphericity. Position is the location of an object in relation to a point of reference. Perimeter is the length that surrounds an area of an object.

The numerical values in FIG. 6 are the average of a sample set comprised of all witnessed object orientations for each particle shape (rows) and each method (columns).

FIG. 6 (Column A) Circumscribed: The circumscribing circle method approximates the apparent frontal area of an object by finding the smallest circle that can entirely enclose the object. The diameter of the circle is used to calculate the individual object volume ($V_i$) of an equivalently sized sphere, as defined by:

$$V_i = \frac{4}{3}\pi r^3$$

where r is the radius. Similar to this method is the inscribed circle method that approximates an object area by finding the smallest circle that can be enclosed by the object. An inherent flaw of both methods is they do not account for porosity or other measures of object irregularity. Either method uses only a single geometric property in its calculation. Because of the assumption of a near spherical object geometry, the circumscribed method will always be erroneously large while inscribed will always report too small.

FIG. 6 (Column B) Heywood: The Heywood, or equivalent area circle, volume estimation method is based solely upon the apparent frontal area from a particle. The volume of a sphere with equal apparent frontal area to the object is calculated and assumed equivalent to the volume of the observed particle. The output of this method is independent of changes in particle porosity and uses only a single geometric property in its calculation. In this method the individual object volume ($V_i$) is defined by:

$$V_i = \frac{4}{3}\pi \left(\frac{A}{\pi}\right)^{\frac{3}{2}}$$

FIG. 6 (Column C) Pappus: A method for estimating the volume of observed particles based on two geometric properties in its calculation is employed based on Pappus's theorem. In this case, the volume is found by bisecting the observed object through its centroid such that the bisection results in two halves of equal area $$\left(\frac{A}{2}\right).$$

One half is selected and its geometric centroid (X) is calculated. The individual object volume ($V_i$) is defined by:

$$V_i = \pi A X$$

FIG. 6 (Column D) Hydraulic: The hydraulic volume estimation method is dependent on two geometric properties in its calculation, the observed particle's apparent frontal area (A) and perimeter (P), and is consequently sensitive to particle porosity. The hydraulic volume is derived from the manning formula, which commonly is used in flow-based calculations. Particles with higher porosity will result in a lower volume estimation output from this method. Conversely, lower porosity will result in a higher volume estimation output for a given area. The individual object volume ($V_i$) is defined by:

$$V_i = \frac{4}{3}\pi \left(\frac{A}{P}\right)^3$$

FIG. 6 (Column E) Heywood-Hydraulic: The Heywood-Hydraulic volume estimation method calculates the average of the output of the two individual methods. This method was developed here because it was reasoned that the hydraulic method is sensitive to porosity and the Heywood method is not, the combination of the two methods often outputs a value that is significantly closer to the true volume of the observed particle. This method also requires two geometric properties in its calculation and demonstrates consistent accuracy.

Floc particles are often highly irregular three-dimensional shapes and as a result, the apparent frontal area of a particle can vary significantly depending on the orientation of the particle from one observation to the next. This was evident throughout the simulation across all shapes (rows) and methods (columns) tributary to the values (averages) tabulated in FIG. 6. In order to more accurately estimate particle volume based upon 2-D imaging the present invention takes particle image data from multiple observations as a given particle moves and changes orientation within the suspending fluid medium. The present invention can use at least 3 samples, at least 5 samples, at least 10 samples, at least 25 samples, at least 50 samples, at least 100 samples, and at least 200 samples.

The analysis reflected in FIG. 6 lead to important conclusions regarding computing particle volume based upon 2-D imaging:

First, though the Heywood-hydraulic method generally results in the closest approximation of true volume (8 of 9) this is not the case for all shapes examined. FIG. 6 (row VI) shows the results of an object where the Pappus method provides a closer approximation than the other methods. This demonstrates the need for a volume estimation methodology to be adaptive and capable of selecting the most appropriate method for consistently achieving the most valid volume estimating method. Second, the results also demonstrate that methods using only a single geometric property are insufficient for producing accurate approximations. Therefore, methods using fewer than two geometric properties in their calculation, such as the circumscribed and Heywood methods, can be explicitly excluded from the system.

Third, in order to achieve improved particle volume estimation results, multiple images need to be analyzed.

FIG. 7 depicts two alternative embodiments using two alternative variants of the illumination assembly 114 means and an optional floc sample volume defining means. Only elements differing from those of FIG. 3 are discussed below.

Figure 7A:
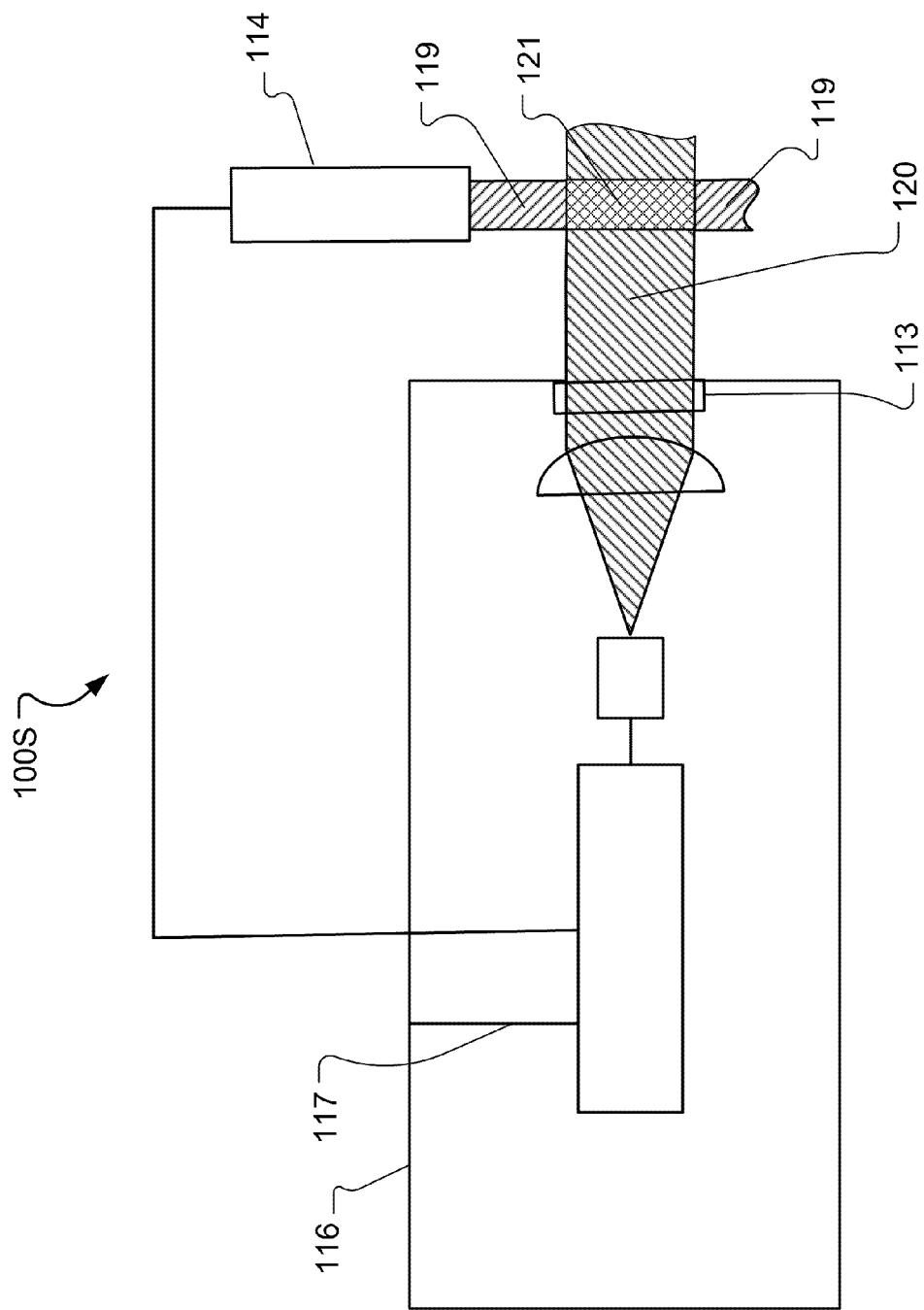
FIGS. 7A-B and 8A-J are schematic views showing alternative embodiments and constructions of the suspended particle characterization system.

FIG. 7A illustrates the illumination assembly 114 as a collimated light source deployed externally to the housing 116. The collimated source may be from a laser source or from a non-collimated source passing through a collimating means consisting of a series of slots, a homogenizing rod, or anything similar understood by someone skilled in the art. This alternative embodiment allows the system 100 body and the illumination assembly 114 to be mounted or moved independently. This configuration allows the sample volume 121 to be located remotely from the optical window 113. This embodiment has multiple benefits. First, it allows for fabrication of a system with no surface features nearby the window 113, thereby reducing any potential floc particle disruption due to protruding elements. Second, it provides for the opportunity to mount the sensor in a fashion where no optical surface touches the liquid (see FIGS. 8E and 8F). This allows the system 100 to monitor floc in liquid containing solutes with strong tendencies to foul optical surfaces that would render more traditional configurations functionless.

Figure 7B:
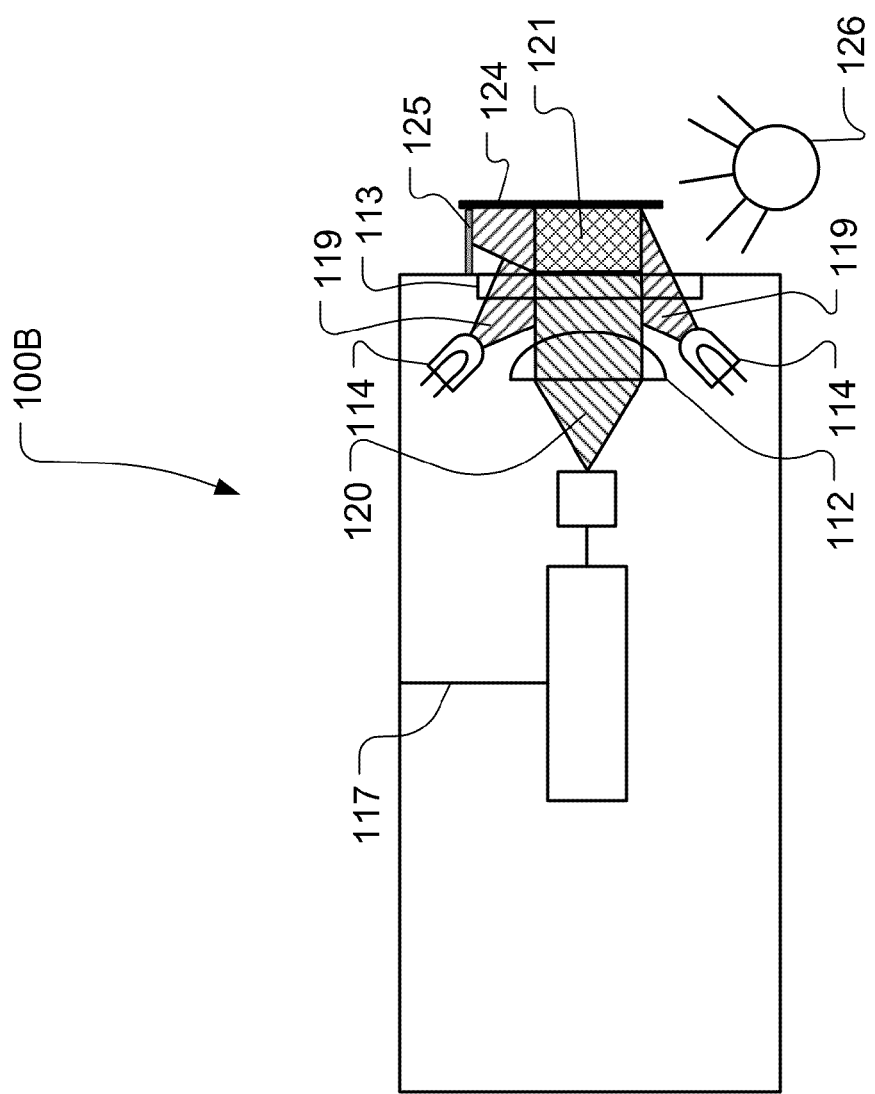

FIG. 7B illustrates the illumination assembly 114 as a non-collimated, multi-sourced light supply deployed around the optics 112, emitting light through the optical window 113 involving multiple intersecting illumination volume 119 elements that also intersect with the optical view volume 120 thereby forming a sample volume 121. FIG. 7B illustrates how such a different illumination method can be used effectively when combined with additional elements. Use of a contrast plate 124 connected by legs 125 to the optical window 113 face is used in this configuration to improve floc particle image contrast and to provide the final boundary plane for the sample volume 121 defining means. This embodiment, particle characterization system 100B, simplifies construction, maintenance, improves reliability and complexity of the system 100 while improving contrast for use in lower reflectivity particle environments.

FIG. 8 represents several alternative embodiments of the particle characterization system 100 deployed in alternative ways, described in detail below.

Figure 8A:
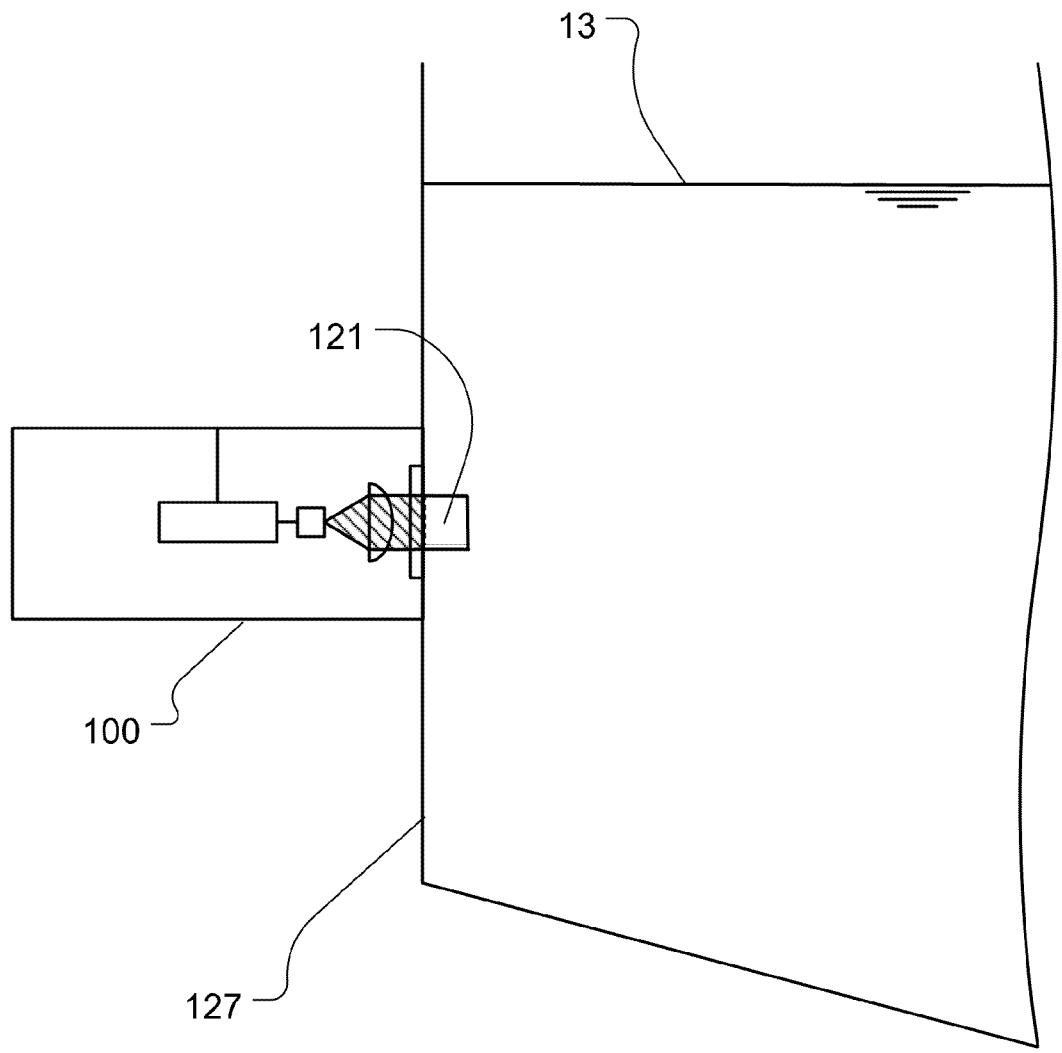

FIG. 8A shows the system 100 attached flush to the wall of a vessel 127 but with the sample volume 121 protruding into the coagulated liquid 13. This deployment offers only minimal prospect for disruption of floc particle characteristics. This embodiment can function in continuous-flow sample mode if the vessel 127 is placed in process with continuous inflow and outflow. If the inflow and outflows are stopped, this embodiment can also function in batch sample mode.

Figure 8B:
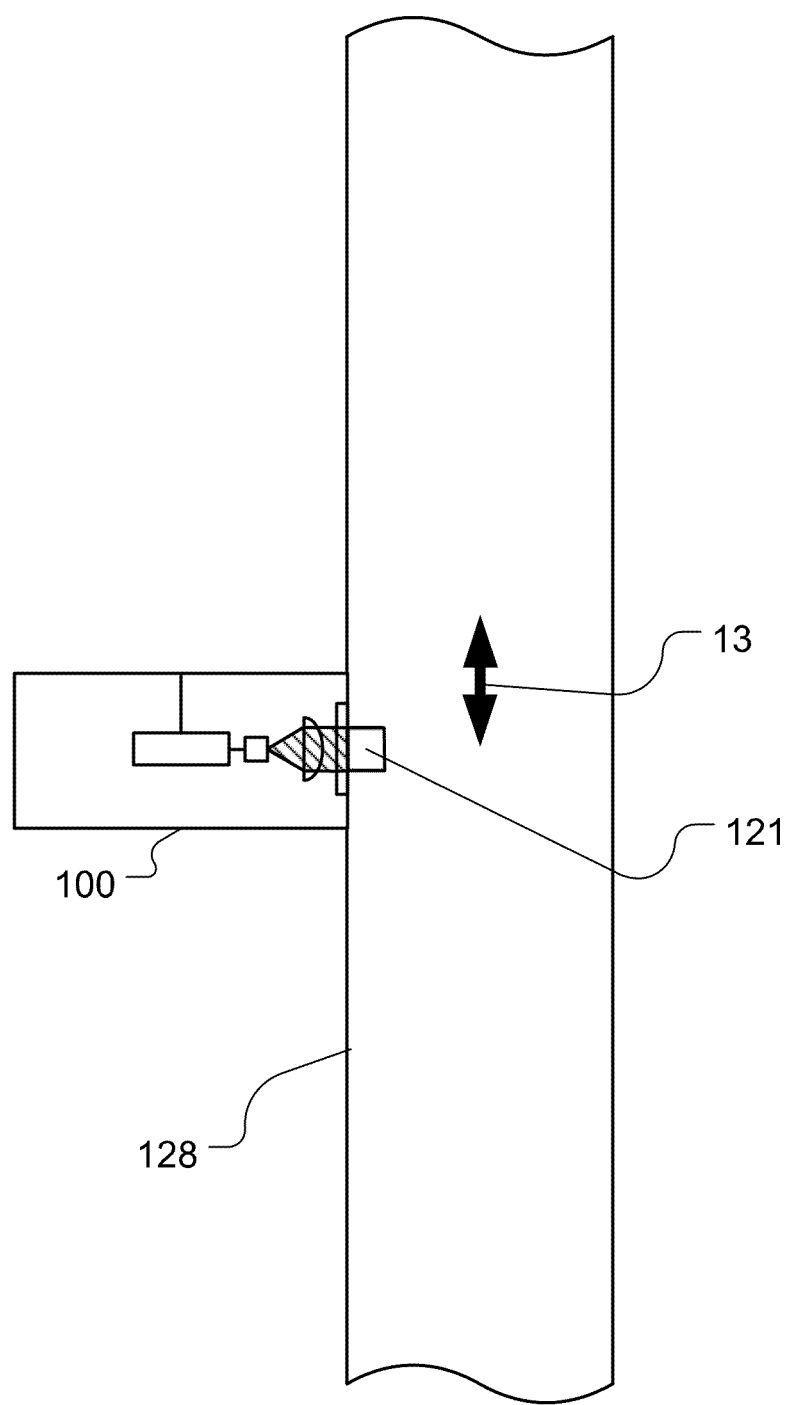

FIG. 8B depicts the system 100 mounted to a conduit 128 through which a coagulated liquid 13 is flowing. This embodiment is fabricated such that only the sample volume 121 protrudes into the conduit 128 thereby producing the minimum disturbance of suspended particle movement. The conduit 128 can be a pipe, a pipe section, an open channel, processing means, or anything similar that can be understood by someone skilled in the art. When the coagulated liquid 13 is flowing, the system 100 operates in continuous-flow mode. When the flow is blocked, the system 100 operates in batch sample mode. If the turbulence ceases in the isolated liquid 13, the fluid enters the settling environment regime allowing for the measurement of particle gravitational settling velocity.

Figure 8C:
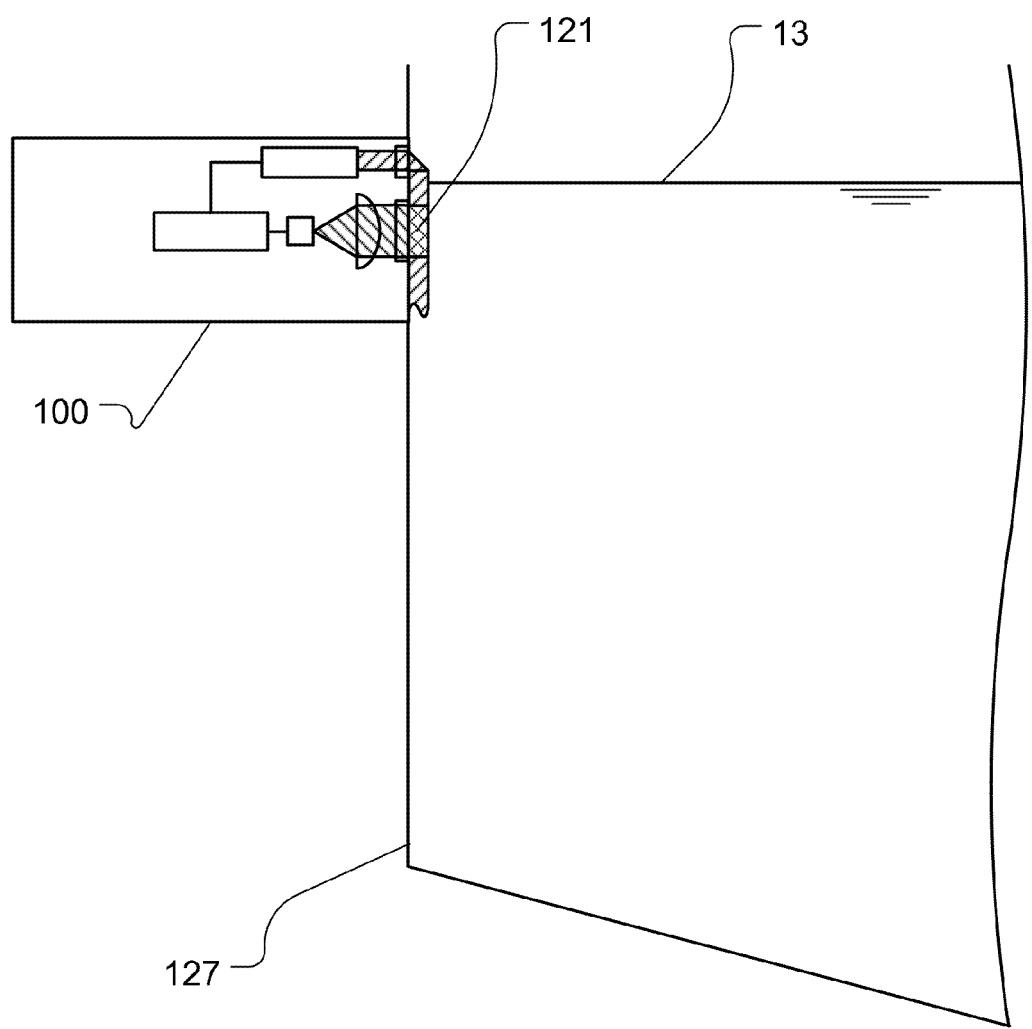

FIG. 8C depicts the particle characterization system mounted in an open vessel 127 wall at a location such that the optical prism 123 is located above the air-liquid interface but the sample volume 121 remains in the coagulated liquid 13. This arrangement provides an uninterrupted flow of floc sample into the sample volume 121 representing the minimum potential for system 100 physical design features, such as baffle plates, to disrupt floc physical characteristics.

Figure 8D:
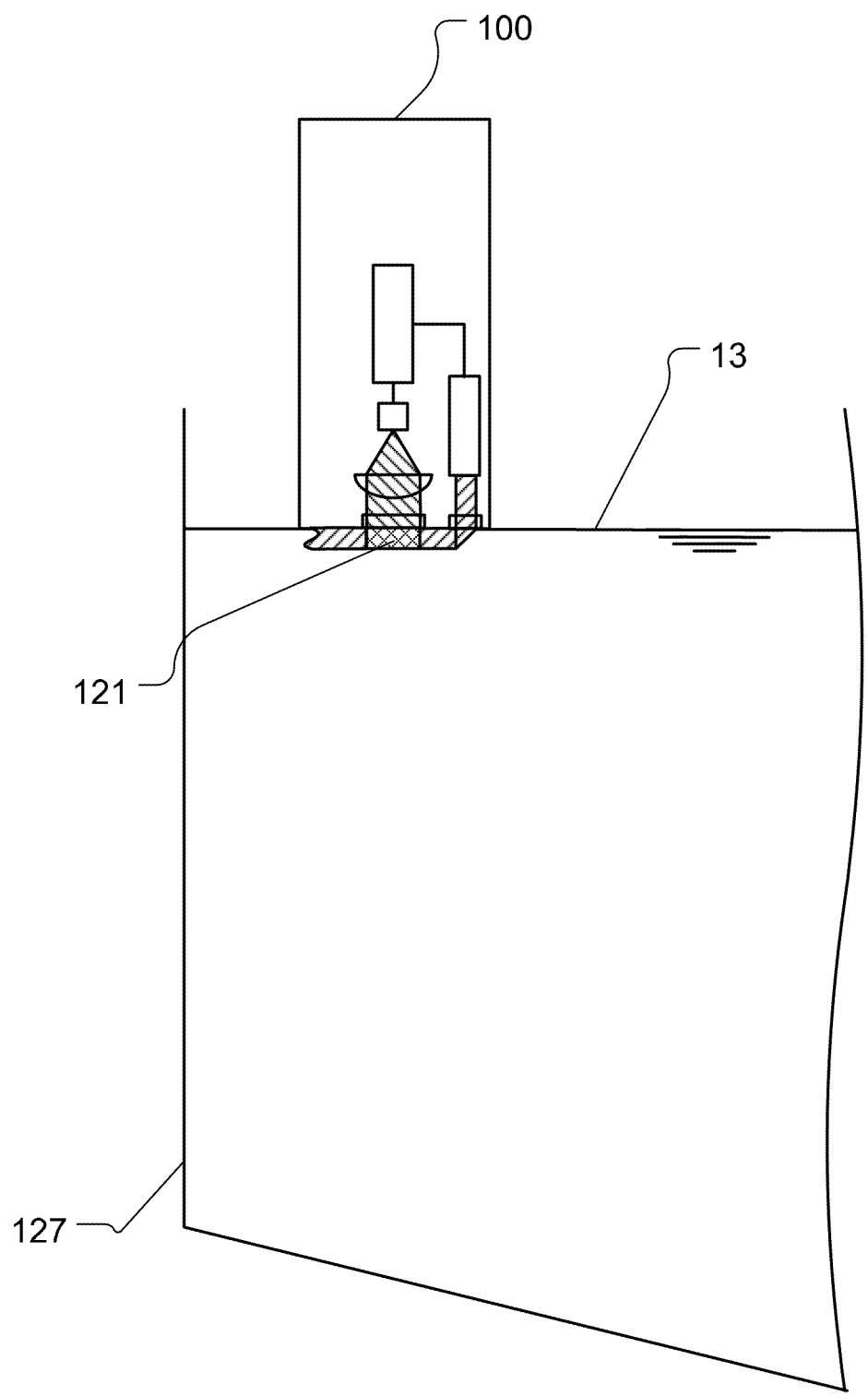

FIG. 8D depicts the system 100 mounted vertically at the air-liquid interface with the sample volume 121 protruding into the coagulated liquid 13.

Figure 8E:
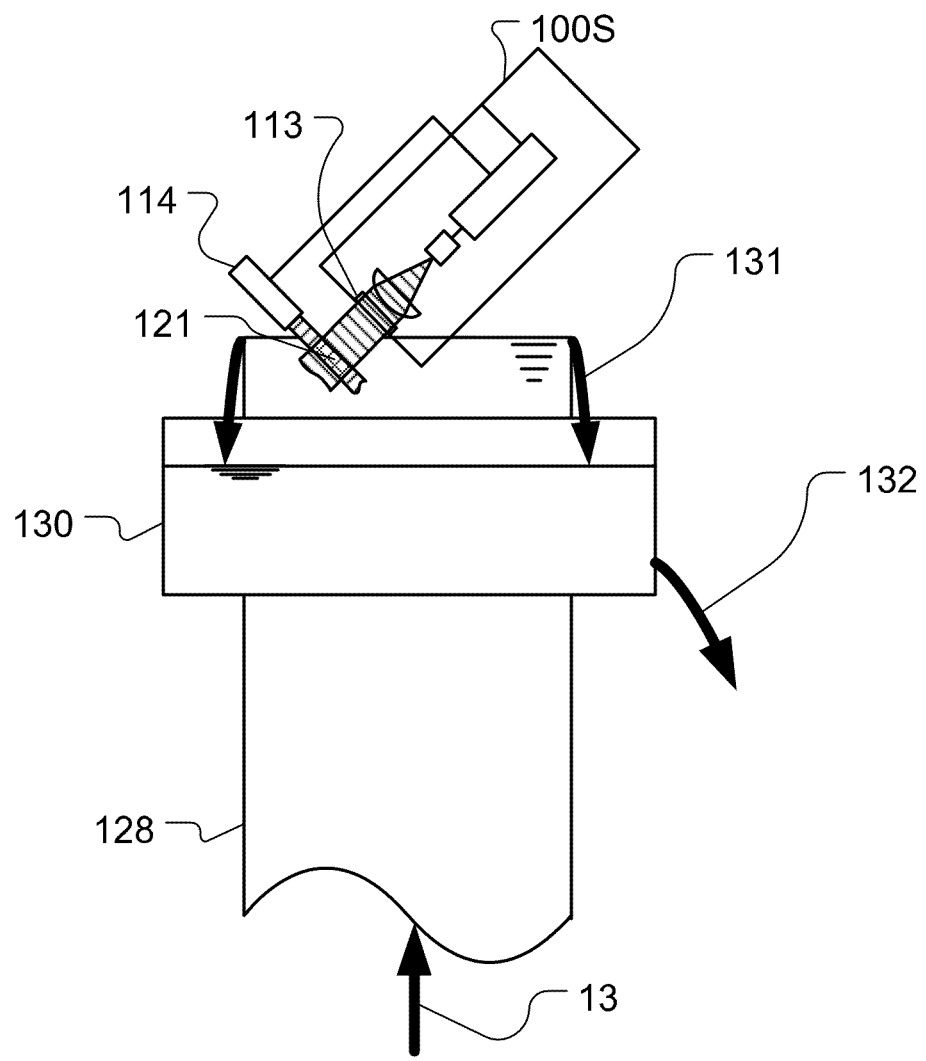
Figure 8F:
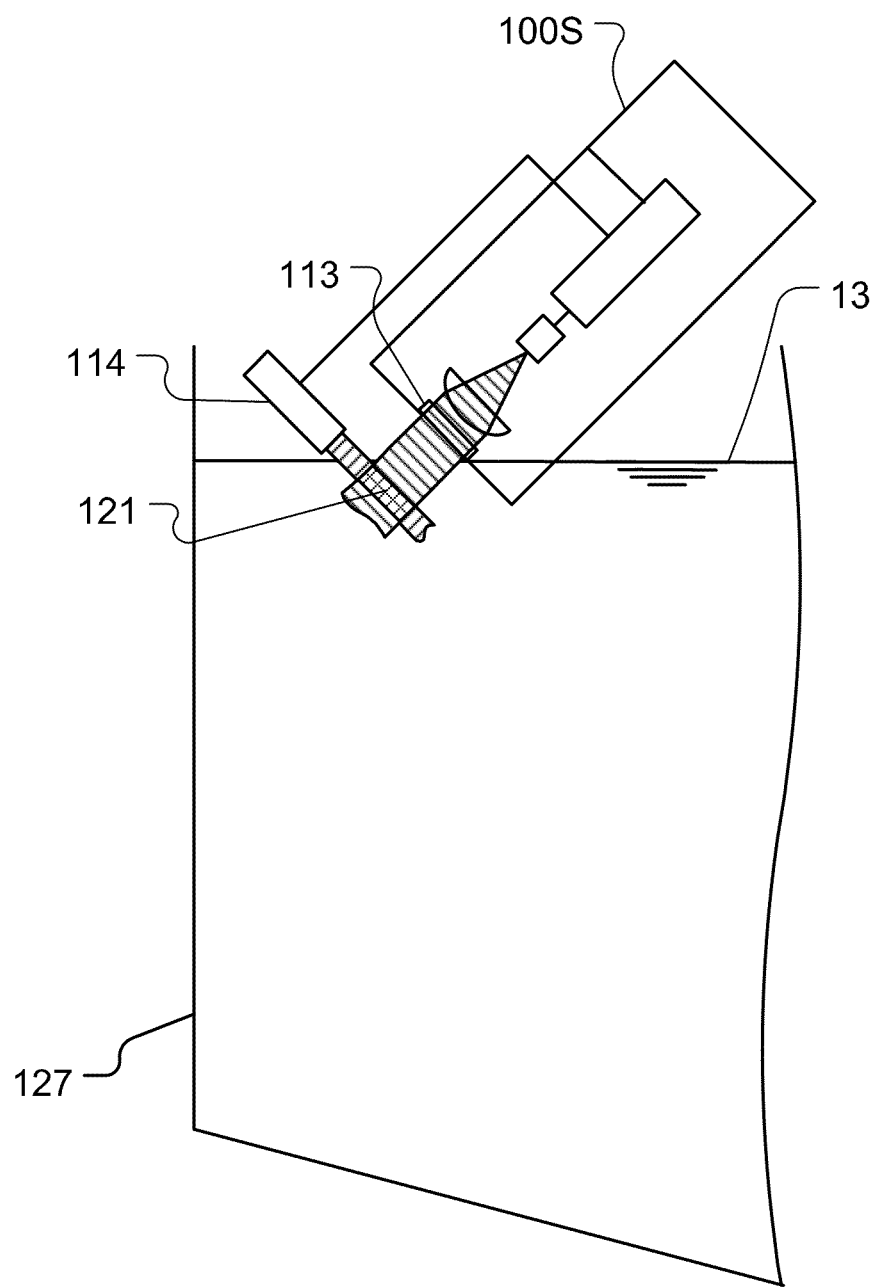

FIGS. 8E and 8F shows the system 100S deployed above the air-liquid interface without either optical surface touching the liquid. The configuration of elements illustrates the sample volume 121 located below the gas-coagulated liquid 13 interface in both embodiments. This allows streams containing surface fouling constituents such as fats, oils, and greases to be analyzed without interferences arising from fouling of the optical illumination and image acquisition surfaces. Due to the need for continuous refreshment, the system 100S depicted in FIG. 8E can operate only in continuous-flow mode whereas the device in FIG. 8F can operate under either mode.

In FIG. 8E the system 100S is mounted above an open-ended variant of a conduit 128 showing a catchment stream overflow 131 into a chamber 130 with a stream to waste 132. This configuration provides the coagulated liquid 13 up-flow in a continuous stream into the sample volume 121, while avoiding contact with any sensor physical components 113 and 114. This embodiment allows for continuous measurement in a flow stream of $V_c$, $N_c$, and $D_s$ which has the advantages of:

(i) Reducing floc characteristic errors resulting from sensor optical surface fouling;
(ii) Reduced maintenance frequency, and;
(iii) Increased reliability.

Figure 8G:
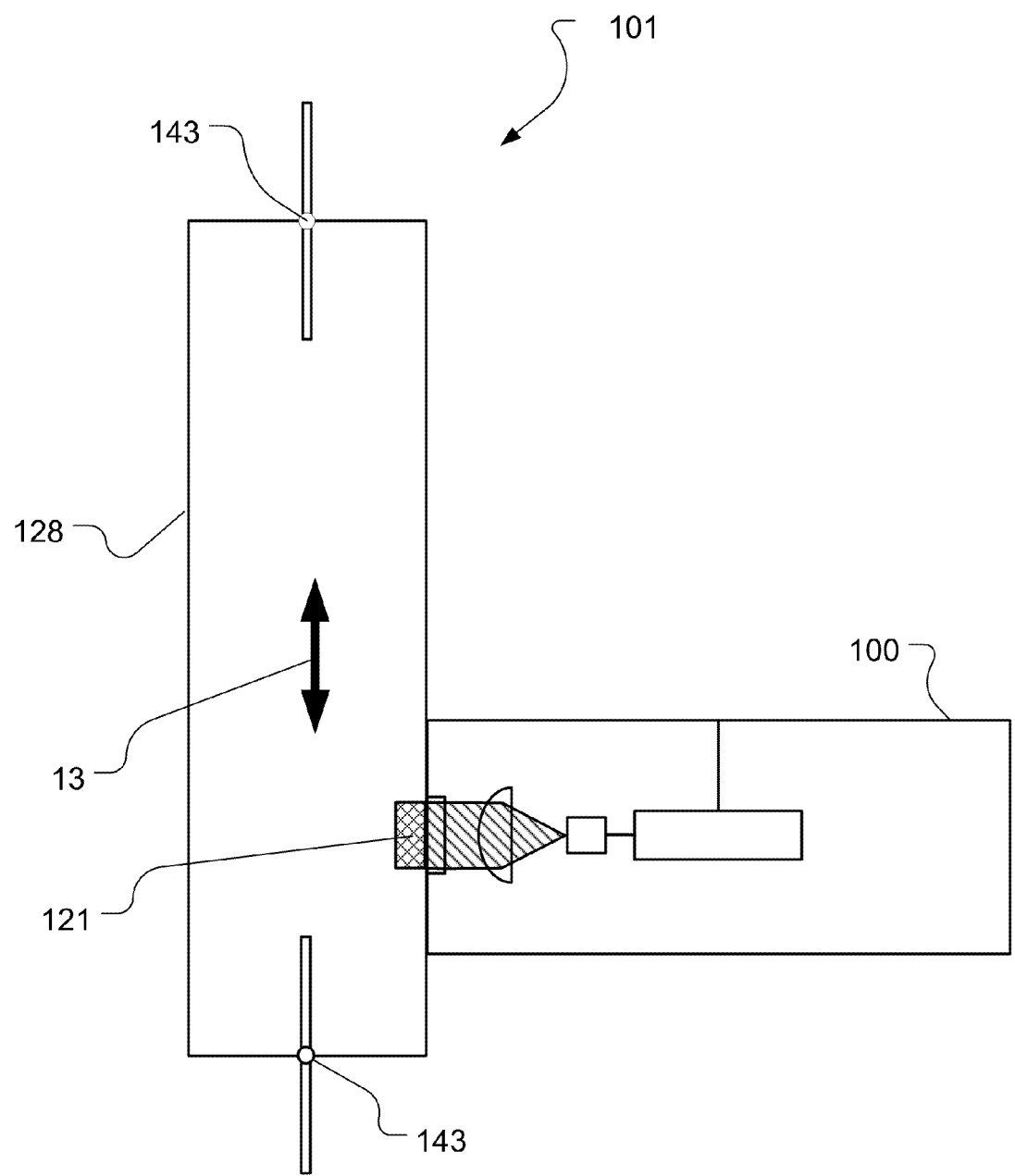

FIG. 8G depicts an alternative embodiment of system 100 designated as suspended particle characterization and turbulence control system 101. This embodiment is composed of system 100 attached to a conduit section 128 with valves 143 located on either side of system 100 with only the sample volume 121 extending into the coagulated liquid 13. This configuration 101 can operate in continuous-flow sample mode when the liquid 13 is flowing or in batch sample mode when the valves 143 are closed. Closing the valves 143 allows the system 100 to monitor particle characteristics in a settling environment inside the vessel 128.

Figure 8H:
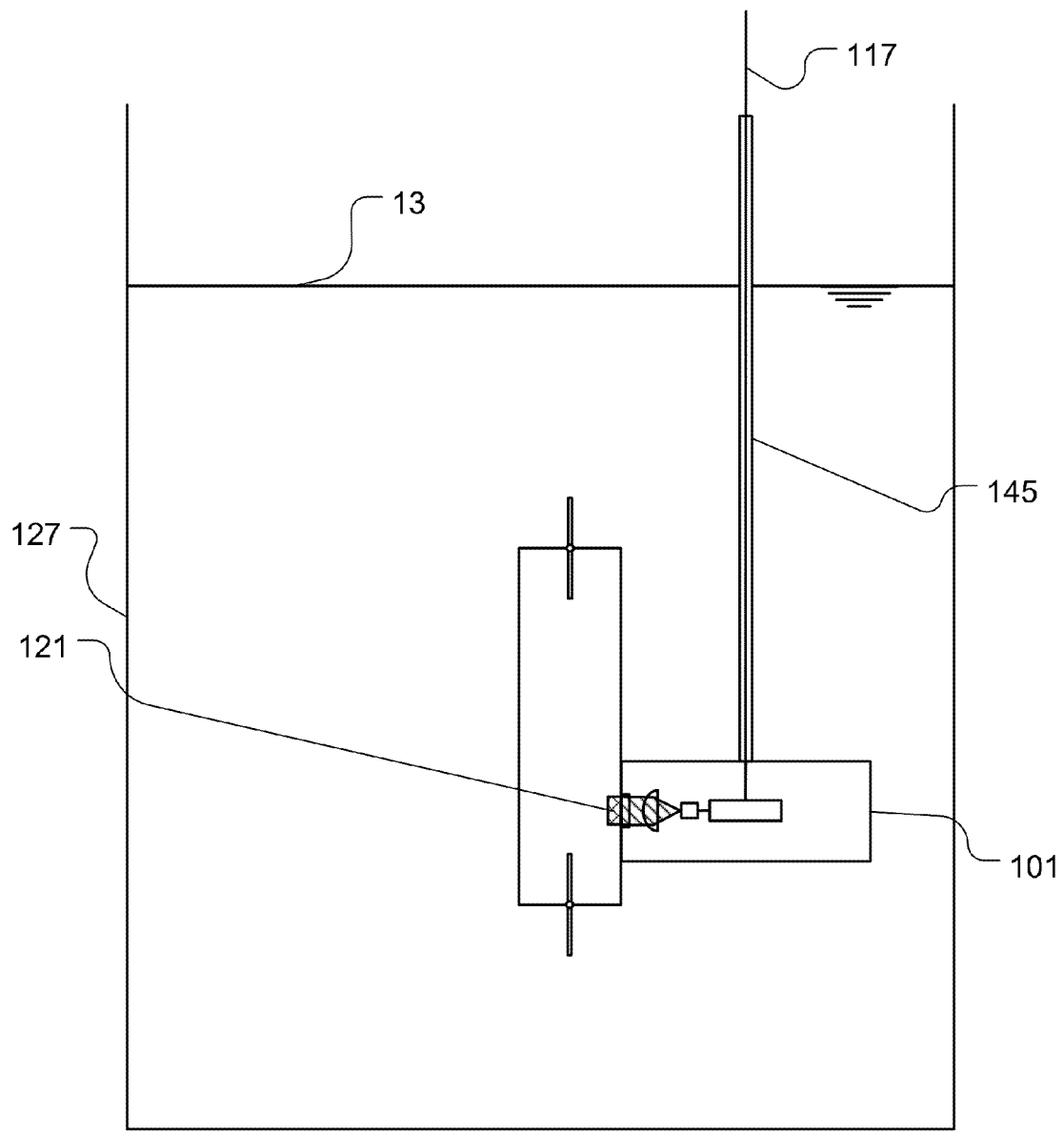

FIG. 8H depicts system 101 suspended by a placement means 145 and immersed in a large vessel 127 containing coagulated liquid 13. The vessel may also be equipped with turbulence introducing means to induce floc formation and growth but prevent reliable measurement of gravitational settling related suspended particle characteristics such as $V_g$, $\rho$, and $M_c$. The system 101 can be operated in a continuous-flow sample mode for measuring $V_c$, $N_c$, and $D_s$ over a period in batch sample mode measuring a full compliment of variables. Embodiment system 101 can be immersed into any location in a vessel, conduit, processing system locations 13A-13D, 16A-16D, 17A, 17D, side-stream from said locations or anything similar that can be understood by someone skilled in the art.

Figure 8I:
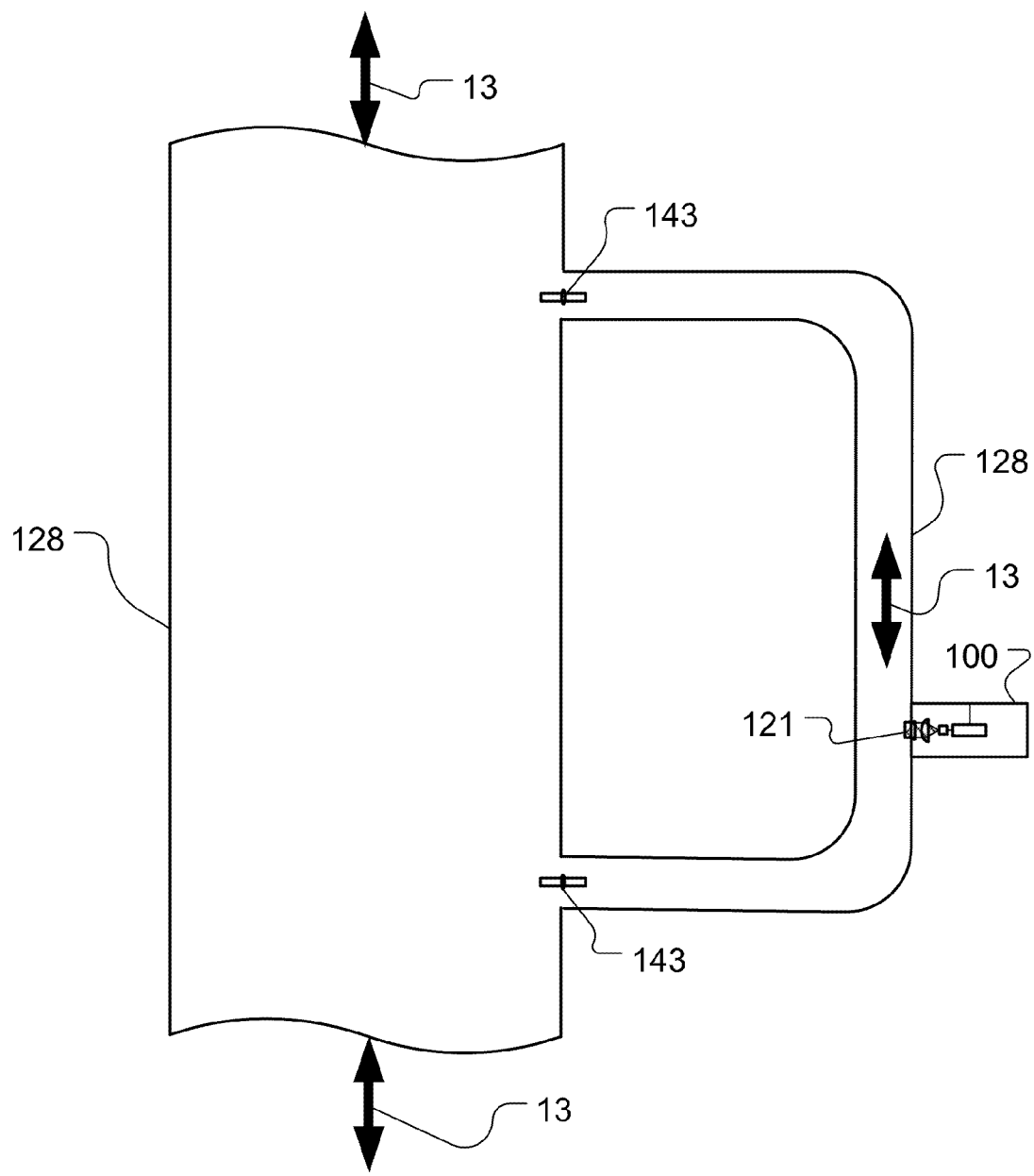

FIG. 8I depicts the system 100 attached to a conduit 128 configured with two parallel paths. The valves 143 can isolate the fluid path where the system 100 is mounted. This allows the system 100 to operate in continuous-flow sample mode or in batch sample mode without interfering with the overall transport of the liquid 13 in the conduit 128.

Figure 8J:
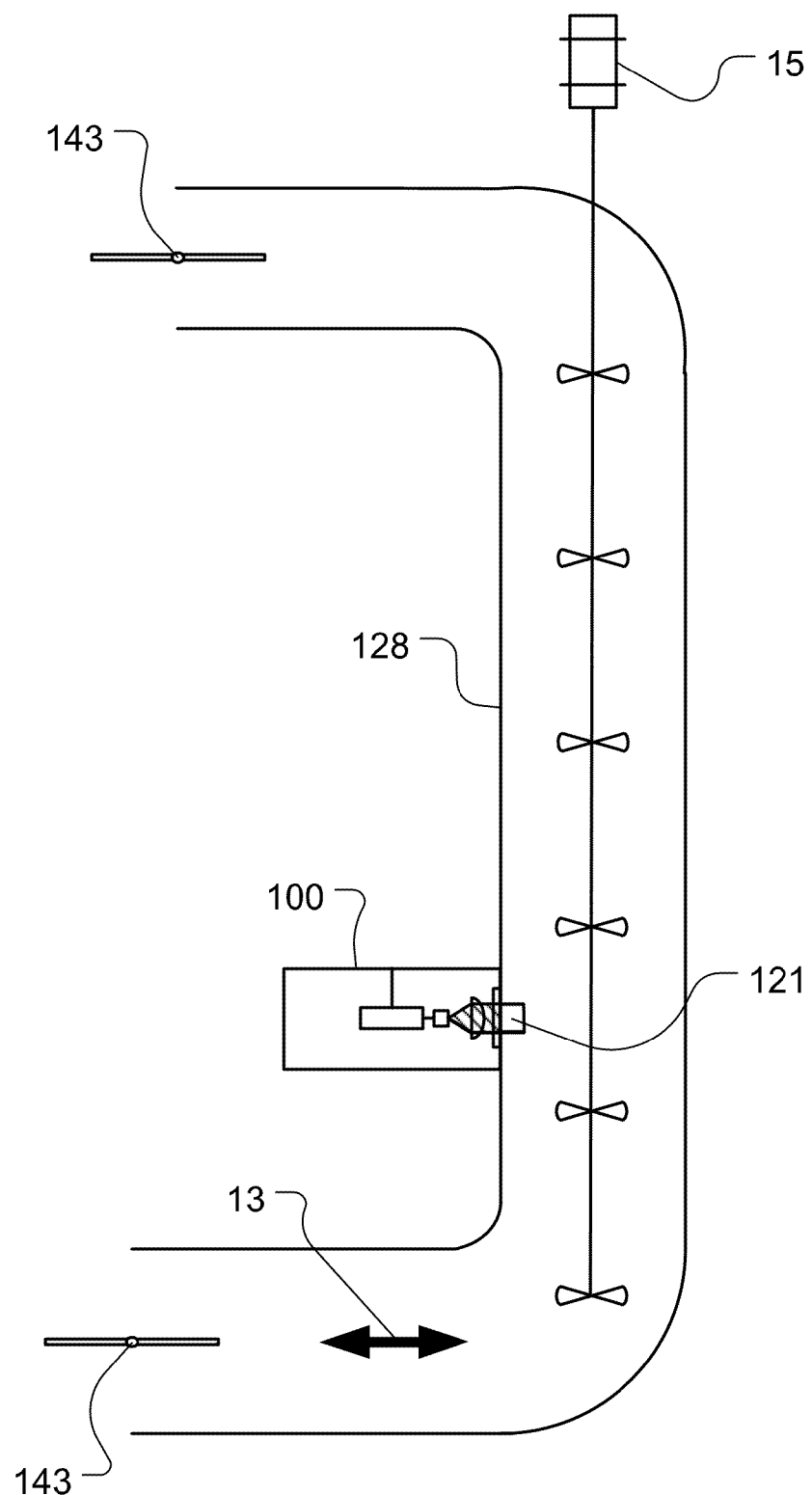

FIG. 8J depicts another alternative embodiment for deployment of system 100 attached to a conduit 128, combined with valves 143, and with a mixing means 15. If the coagulated liquid 13 is turbulently mixed while in batch sample mode, floc-particle characteristics can be analyzed against variables such as mixing time, and mixing intensity. Settling conditions can occur if the mixing is stopped allowing for measurements related to gravitational settling to be taken and analyzed.

Figure 9:
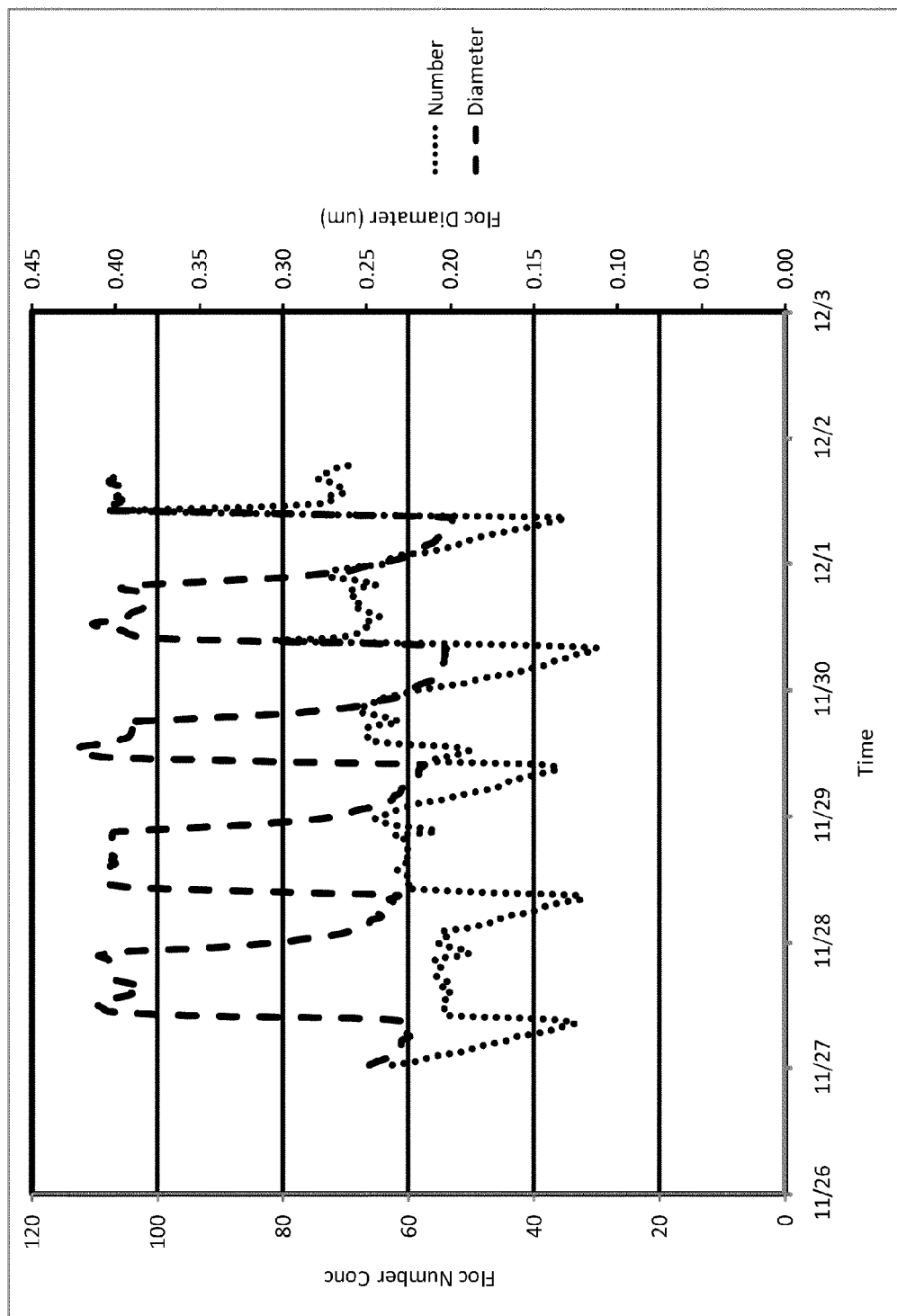
FIG. 9 is a graph used for explaining the importance of mass density in water treatment processing.

FIG. 9 is a graphic representation of floc-particle analysis results from an operating water filtration plant demonstrating the significance of floc-particle mass density, discussed below.

FIG. 9 is constructed from floc particle analysis at a conventional coagulation-flocculation-plate-settler-filtration plant using a development system similar to system 100 located near the floc tank exit. The graph reflects a repeated diurnal pattern over 4.5 day period showing that floc particle diameter and particle count both decrease by ~½ from daytime to nighttime operation.

During testing, the plant operated as a normal facility during the daytime, during which raw water is coagulated-flocculated-settled and filtered at a constant continuous flow rate through the floc chamber and the entire treatment process. The daytime operation is continuous flow through three mechanically mixed floc reactor basins separated by baffle plates. At nighttime, only the flocculation-stir motors ran; no newly coagulated water inflows into the floc chambers, and no product flows from the floc reactor to the plate settlers. Effectively, the nighttime operation is batch floc processing being performed on a large sample of water formed by continuous-flow coagulation-flocculation processing. The total floc-particle mass remained constant during this period.

A reduction in floc diameter at night, presumably by breakup, should lead to an increase in particle count if mass density were assumed constant. FIG. 9 demonstrates an opposite trend meaning mass density of the particle must be changing in order to preserve total system mass in addition to or instead of breakup.

Floc mass density change is the most logical alternative to the prospect of floc breakup. If one combines reactor theory with the assumption that the floc reactor design details and actual operation performance of this particular facility may be less than ideal, it can lead to the following scenario. This batch-mode reaction approaches an ideal processing scenario where all floc experience similar mixing induced fluid-shear history. Consequently, a more uniform tightly packed particle distribution develops over time. To the contrary, the daytime continuous flow-mode processing, combined with the necessity that mixing is mild (far short of the ideal situation of a completely mixed tank reactor) introduces opportunities for fluid short-circuiting (read, increased number concentration of small floc resulting from shorter residence time and fewer floc-floc collision opportunities). This mild mixing, which is necessary to avoid floc shear, also provides ample opportunities for dead zones, especially in a rectangular reactors, that can lead to the formation of very large loosely-packed floc. The net result of such non-ideal continuous-flow processing as described above lends qualitative support for the trends showing high number concentrations and with both smaller and larger size floc and reduced mass density.

The implications of FIG. 9 are:

Two variables of floc particle characteristics, diameter and count, are inadequate to account for physical characteristic variation of floc particles, e.g., by >100%

Knowing floc-particle mass density is essential to fully characterize floc formation in water-separation processing.

Figure 10:
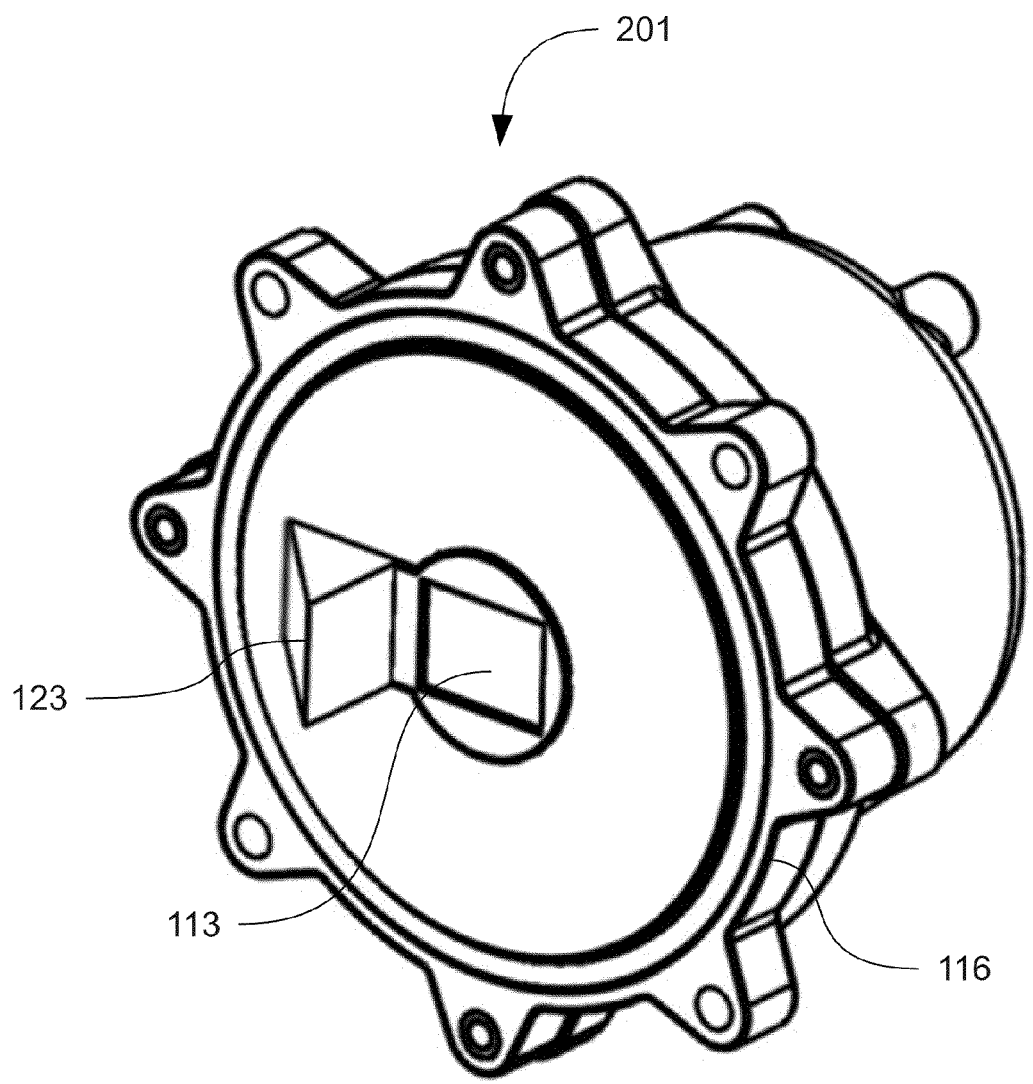
FIG. 10 is an isometric rendering of the present invention.

FIG. 10 is a three-dimensional rendering of the system 100.

The rendering 201 is an isometric view of the system 100. External elements can be seen here. Such elements include the prism 123, window 113 installed in housing 116. This view is provided to aid in further understanding the construction of the system 100. This illustrates the minimal obstructions surrounding the sensing face and the convenience for alternative placement in-situ or for mounting to a vessel 127 or conduit 128 wall.

Figure 11:
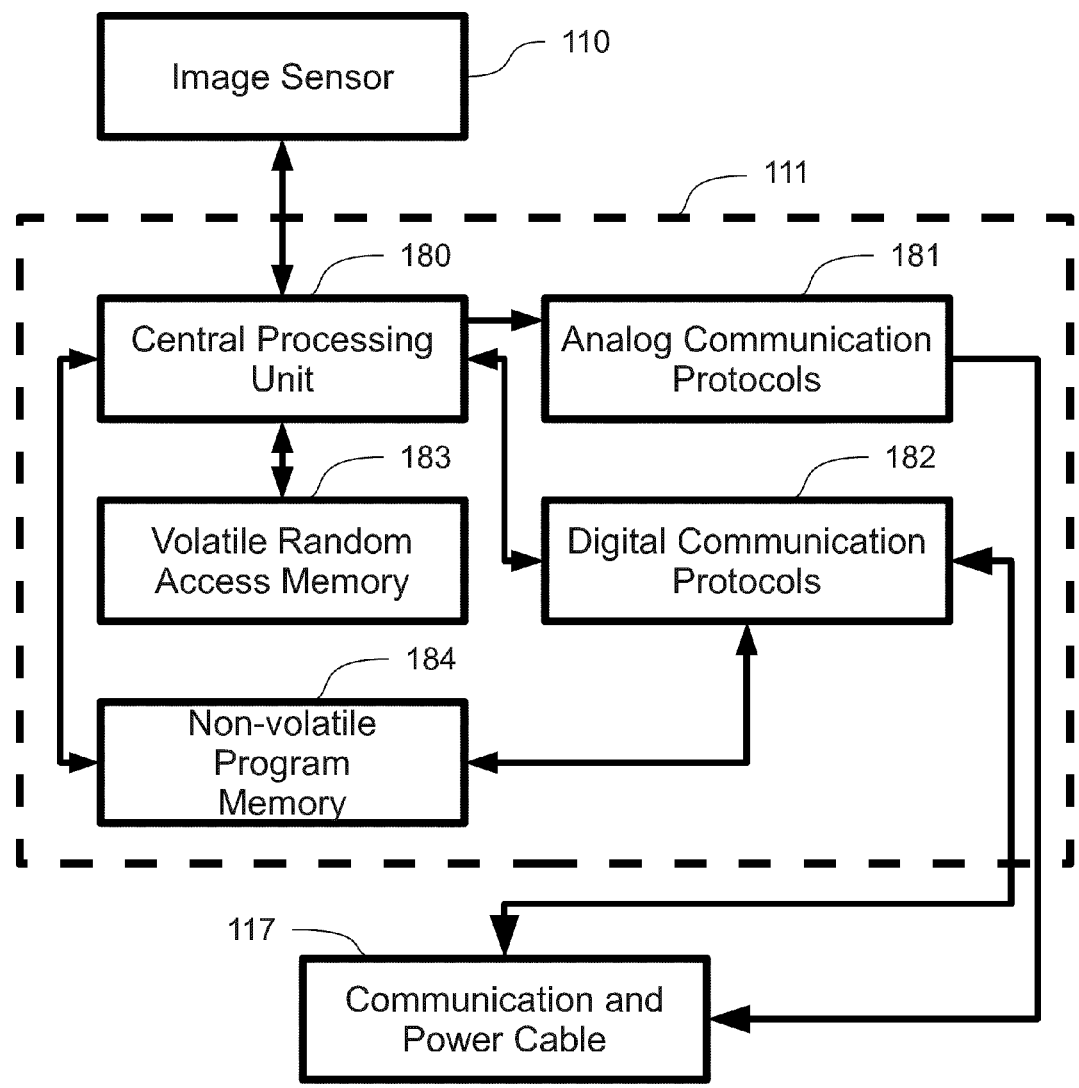
FIG. 11 is a block diagram of a computing engine.

FIG. 11 depicts a system diagram of the computing engine of system 100, described below.

The central processing unit 180 is comprised of an electronic circuit that can execute computer programs. The central processing unit 180 can be any application specific integrated circuit, microcontroller, general-purpose microprocessor, field programmable gate array, or similar device understood by someone skilled in the art. The central processing unit 180 reads and executes computer programs stored in non-volatile program memory 184. The non-volatile program memory 184 can consist of, but is not limited to electrically erasable programmable read-only memory, magneto resistive random access memory, or flash memory. The non-volatile program memory 184 stores the computer program data that is used by system 100 to perform all major logic and communication functions, and can be used to archive measurement data and system configuration data. The non-volatile program memory 184 can retain the stored data when the system is not powered. The data stored on the non-volatile program memory 184 can be remotely accessed and modified via digital communication protocols 182 in order to upgrade system software or otherwise alter system behavior. Digital communication protocols 182 can include but are not limited to TCP/IP, RS-232, USB, or wireless protocols such as IEEE 802.11 and Bluetooth. The non-volatile program memory 184 can be remotely accessed through digital communication protocols 182 directly, or through the central processing unit 180 as an intermediate device in a data-link layer.

During normal system operating, the central processing unit 180 receives image data from the image sensor 110, as discussed in the description of FIG. 4. The central processing unit 180 uses the volatile random access memory 183 for short term of data such as images, programs, and particle measurements. The data stored on volatile random access memory 183 is only retained when the system is powered on. The volatile random access memory 183 can consist of: but is not limited to dynamic random access memory or static random access memory. The volatile random access memory 183 may be physically integrated with the central processing unit 180 hardware.

The central processing unit 180 can output data to analog communication protocols 181 though digital to analog conversion hardware. Analog communication protocols 181 can be used to communicate with external devices, such as SCADA networks, programmable logic controllers, data loggers, and alarms. Analog communication protocols 181 can include but are not limited to current loop signals, voltage signals, and frequency or amplitude modulation signals.

Figure 12:
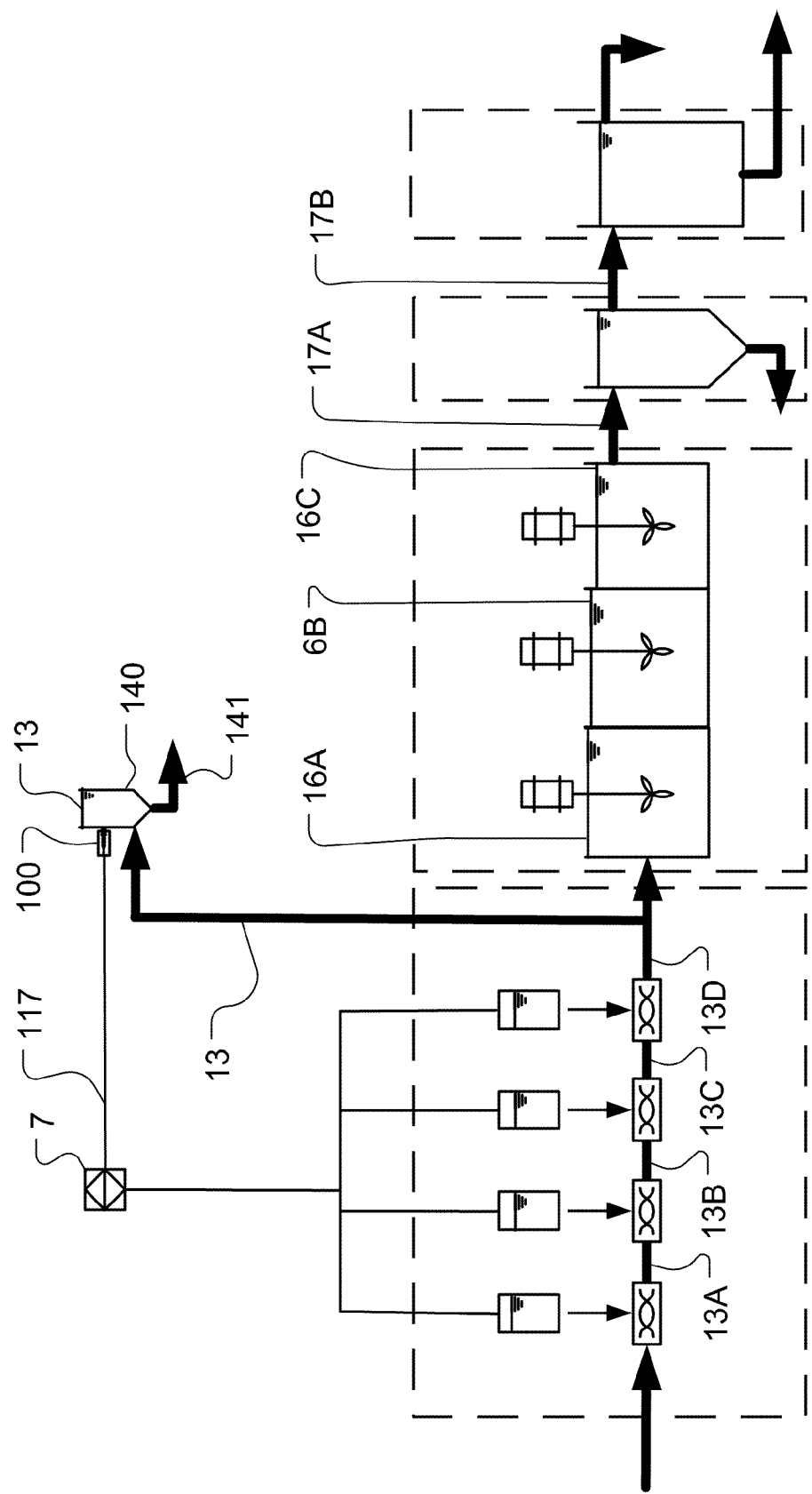
FIG. 12 is a schematic view of the preferred embodiment deployed in a side-stream location.

FIG. 12 depicts a water treatment processing system similar to FIG. 1. The two water treatment systems differ in the deployment of system 100. The differences gives rise to major changes in the information collected for characterizing, optimizing, and control of each specific water treatment processing system. More significantly, it changes information tendered to plant operators thereby enabling proactive process optimization and control at a manageable level of risk to full-process performance.

In the case of FIG. 1 all the information collected by the system 100 is tied to the time, chemical, and physical domains of the full-processing system because changes in coagulant dosage must first propagate through the full-processing system before they can be detected and measured to aid in control decisions.

In the case of FIG. 12 however, all the information collected by the system 100 is effectively independent of the time, chemical, and physical domains of the full-processing system, if the system is operated as described below. This means that all three domains can be explored, reconnoitered, and mapped without risk to the quality of the full process product water. This empirical information can provide a broader range of information for plant operators to make decisions in the operation of the full process. Since this system is side-stream and independent of the time domain of the full process, it can be exploited as a pilot system, with the inherent low risk to full-process quality, while simultaneously achieving:

(i) Near real-time, ad hoc feedback for process optimization and control of both coagulation chemistry and flocculation mixing regime.
(ii) Freedom to reconnoiter operationally-controllable-variable-floc response empirically, ad hoc with exacting coagulation-chemical similitude.
(iii) Employing a near ideal surrogate variable reflecting pollutant removal success.

The embodiment depicted in FIG. 12 collects coagulated liquid 13 downstream of coagulant addition points and uses the system 100 to analyze the samples. This configuration reduces the risk of compromising full-process-effluent quality. The combined system consists of a batch sample mode side-stream sample processing system 140 unit, similar to FIG. 8A system, with an attached system 100, an input control mechanism that receives freshly coagulated full-process stream samples 13, a sample discharge control valve, and a fresh water spray system for reactor cleaning and preparation. The attached system 100 measures particle characteristics as discussed in the description of FIG. 4 and FIG. 5. This includes either floc formation data set $V_c$, $N_c$, and $D_s$ during mixing, or intermittent data sets of $V_c$, $N_c$, $D_s$, $v_g$, $\rho$, and $M_c$ available follow cessation of mixing. The data output of the system 100 can be used by external hardware to drive a control system for the optimization and control of full process coagulation dosage and mixing motor behavior. Such a control system can be used for all routine testing including the initial operation performed at startup for a new site for local optimization. The samples can be taken from any point downstream of coagulant addition, such as but not limited to 13A, 13B, 13C, 13D or 16A-16C. The side-stream coagulation-flocculation optimization system can be used to measure the coagulation-flocculation process-feedback response on a shorter time scale than the mainstream of the treatment facility, allowing for more effective optimization and control of the treatment process.

The operation of the side-stream coagulation-flocculation optimization system is a serial process involving multiple steps. First, the sample of coagulated liquid 13 is collected in reactor 140, though the use of valves or other fluid control means 13. The sample is then processed through mixing-flocculation by application of a mixing means. Floc growth is monitored by the system 100, as discussed in the description of FIG. 4 and FIG. 5. The mixing can be temporarily stopped on demand to allow for particle gravitational settling for the measurement of particle density, as discussed in the description of FIG. 5. Finally, when a sample processing cycle is complete the sample is purged by sample to waste 141 means and the reactor is cleaned and prepared for next sample cycle. Subsequently, full-process coagulation 2 mechanism can be used for a brief interval, sufficient to prepare, to divert, and to fill vessel 140 with another exploratory sample, and thence return full-process chemical coagulation to 'normal' settings or temporary changes in flocculation mixing regime. An exploratory sample is prepared by either raising or lowering the full-process dosage of one coagulant chemical species, one at a time, say +/−<10% of the current set point dosage value, for only a brief time period but sufficiently long as defined above. Alternative, an exploratory sample can be prepared by changing full-process mixing regime temporarily. Said reconnaissance sample is then analyzed off-stream of the full process for floc response mapping. This methodology can be repeated as necessary in order to define the local optimum, charge neutral, alternative optimum criteria, or anything similar that can be understood by someone skilled in the art of coagulation chemistry set point value selection. This same methodology can also be used to explicitly quantify if the raw water coagulant demand has changed.

One characteristic of the system depicted in FIG. 12 that must be noted concerns the inability of this or virtually any side-stream system to simulate the physical domain of the full-process system. This approximation cannot be accomplished especially in a practical fashion. However, this limitation is of no significant consequence with respect to facility operation and control. This obtains because of two realities; the chemical and physical domains of coagulation-flocculation-removal processing are nominally independent of each other, and the leverage ratio—for an operator to control pollutant-removal success—is of the order of $10^5:1$ [chemical: physical]. This is to say, if the coagulation chemistry is significantly off optimum, pollutant removal will likely be mediocre at best whereas off-optimum mixing regime has only limited leverage on removal quality, by comparison. Off-optimum operation normally poses limited human health risk because drinking water is also typically disinfected with chlorine following filtration. Chlorination effectively kills virtually all infections organisms, except for Cryptosporidium parvum. Cryptosporidium, though found to be virtually omnipresent in surface water, is rarely present in significant concentrations, in which cases off-optimum coagulation is nominally sufficient to remove most Cryptosporidium at 1.5-log removal. However, in the case of high raw water levels such as the drinking water disaster in Milwaukee, Wis. in 1993, off optimum coagulation, as was apparently the case, results in catastrophic failure. To the contrary, optimum coagulation chemistry, as has been demonstrated, yields near-quantitative removal of cryptosporidium and Giardia, and therefore may be required in cases such as Milwaukee. Recently, drinking water facilities have begun adding expensive processes, such as UV disinfection, which effectively kills cryptosporidium, or replacing granular-media filters with membrane filters. A much less expensive alternative for the worlds' infrastructure of coagulation-granular filtration systems is to employ effective metric based control systems in order to reliably optimize coagulation chemistry—thereby achieving the removal performance potential (e.g., ~5-log removal vs. 1.5-log removal) of such systems, as may be the case for the Partnership Level IV class of facility operation.

Alternative embodiments of the side-stream system (FIG. 12) include but are not limited to the following or anything similar that can be understood by someone skilled in the art including:

(i) A multi-train full processing system with a dedicated coagulation 2 mechanism. Such a system may be employed for wide ranging chemical and physical response testing in cases where the product water can be diverted from blending with the full-process product stream.

(ii) Side-stream system receiving raw water 1 with a dedicated coagulation 2 mechanisms, and batch process as depicted in FIG. 12. Alternatively, a continuous-flow mechanism can be deployed involving flocculation 3 with or without separation process units involving any of the known separation processing units including membranes. Such systems have the added advantage that either global or universe optimization can be exercised with zero risk to the full-process effluent quality performance.

A variety of control methodologies can be used to evaluate the optimum dosage and mixing speeds to meet treatment facility targets, such as PID control, fuzzy logic, or adaptive systems such as neural networks or genetic optimization algorithms. It is anticipated that the optimal control values may change frequently because raw water quality may change due events outside of plant operations control, such as weather events, man-influenced events such as an upstream diversions or discharges. This variation of input water quality necessitates that the side-stream coagulation-flocculation optimization system continuously operate to find ever-changing optimum control outputs.

While the principles of the disclosure have been described above in connection with specific apparatuses and methods, it is to be clearly understood that this description is made only by way of example and not as limitation on the scope of the disclosure.

What is claimed is:

1. A system for characterizing a suspended particle in a water sample in a treatment facility, the system comprising:
   a chamber for receiving the water sample at a point downstream of a chemical addition point wherein the chamber further comprises a first closable valve located at a water entry point to the chamber and a second closable valve located a discharge point from the chamber;
   a controller coupled to the first valve and the second valve wherein the controller sends a control signal that closes the first valve and a control signal that closes the second valve whereby the water sample is isolated and batch sample mode conditions are created in the chamber;
   an imaging element comprising an electro-optical imaging device configured to view the particle in a defined sample volume of the water sample and generate an image signal responsive to an optical image of the particle in the sample volume;
   an electronic circuit coupled to the imaging device wherein the electronic circuit receives the image signal, which conveys a plurality of time-sequential optical images and recorded times when each image was generated; and
   a computing engine configured to process the plurality of time-sequential optical images and recorded times to:
   determine quantifiable values representing an area and a perimeter of the particle;
   determine a first position of the particle in a first time-sequential optical image at a first recorded time wherein said first position further comprises a first horizontal position and a first vertical position;
   track the particle from the first time-sequential image to a second time-sequential optical image at a second recorded time;
   determine a second position of the particle in the second time-sequential optical image wherein said second position further comprises a second horizontal position and a second vertical position;
   compute a vertical displacement from the difference between the second vertical position and the first vertical position;
   compute a horizontal displacement from the difference between the second horizontal position and the first horizontal position;
   compute a time difference between the first recorded time and the second recorded time;
   compute a gravitational settling velocity in response to the vertical displacement and the time difference.

2. The system for characterizing suspended particles in the water sample in the treatment facility as recited in claim 1, wherein:
   the electro-optical imaging device comprises an illumination source and a digital camera;
   the digital camera further comprises a 2-dimensional image sensor array configured to capture a 2-dimensional projection of the particles in the water sample with the signal;
   the plurality of time-sequential optical images correspond to an elapsed time selected from the group comprising shorter than:
   100 milliseconds,
   1,000 milliseconds, or
   10,000 milliseconds;
   the imaging element is mounted in the wall of the chamber; and
   the defined sample volume comprises a region protruding into the chamber.

3. The system as recited in claim 1, wherein the computing engine is further configured to:
   estimate a particle volume from the area and perimeter of the particle and calculate a mass density from the particle volume, the gravitational settling velocity, the density of water, and the viscosity of water.

4. The system as recited in claim 1, wherein the computing engine further comprises a communications element configured to transmit data to other electronic devices using a communications protocol selected from the group comprising:
   a digital serial protocol,
   a parallel digital protocol,
   a serial pulse width modulated protocol,
   a frequency modulated protocol,
   an analog voltage protocol,
   an analog current protocol,
   an internet protocol, or
   a wireless protocol.

5. The system as recited in claim 4, wherein said communications element further comprises an element from the group comprising:
   a control signal transmitting element; or
   an alarm signal transmitting element.

6. The system as recited in claim 1, wherein the system is configured to fit in a volume selected from the group comprising less than:
   20 cubic inches,
   50 cubic inches,
   100 cubic inches,
   200 cubic inches, or
   500 cubic inches.

7. The system as recited in claim 1, wherein said electro-optical imaging device comprises a digitizing array configured to provide a minimum resolution selected from the group comprising greater than:
    500,000 pixels,
    1 million pixels,
    2 million pixels,
    3 million pixels,
    4 million pixels, or
    5 million pixels.

8. The system as recited in claim 1, wherein:
    said imaging element further comprises a computing element that analyses at least one time-sequential optical image to cause manipulation of an adaptive optical element selected from the group comprising:
        a zooming element,
        a focal length adjusting element,
        an optical aperture, or
        a depth of field adjusting element; and
    the system is configured to process images of particles as large as 10 millimeters.

9. The system as recited in claim 1, wherein the system further comprises an illumination element configured to illuminate a volume of the water sample whereby the imaging element can measure to at least one sample characteristics selected from the group comprising:
    particle reflectivity,
    ambient light level,
    image acquisition,
    particle concentration, or
    particle size.

10. The system as recited in claim 1, wherein the system further comprises an optical surface cleaning element.

11. The system as recited in claim 1, wherein the system further comprises a volume defining means configured to define a sample volume selected from the group comprising not more than:
    5 cubic centimeters,
    10 cubic centimeters,
    20 cubic centimeters, or
    100 cubic centimeters.

12. The system as recited in claim 1, wherein the computing engine further comprises an element configured to identify and subtract image data in response to a comparison with previously stored image data.

13. The system as recited in claim 1, wherein said plurality of time-sequential optical images comprises a minimum quantity of images selected from the group comprising at least:
    3 images,
    5 images,
    10 images,
    25 images,
    50 images, or
    100 images.

14. The system as recited in claim 1, wherein the system further comprises a water sample turbulence controlling element wherein the water sample turbulence controlling element further comprises a mixer responsive to the controller and whereby:
    the system can operate in a mixed environment wherein one of the following conditions are met:
        fluid is flowing through the chamber or
        the closeable valves are closed and the turbulence controlling element is turned on;
    the system can operate in a settling environment in which the water turbulence controlling element is turned off, the closeable valves are closed, and the horizontal displacement and the vertical displacement fulfill pre-defined criteria; and
    the system can operate in a transitional environment in which the criteria for the mixed environment and the conditions for the settling environment are not met.

15. A suspended particle density calculation instrument for a water treatment process, the instrument comprising:
    an isolation chamber suitable for placement downstream of a chemical addition point, the chamber comprising a closeable inlet and a closeable outlet that allow the chamber to isolate a water sample;
    a controller coupled to the closeable inlet and the closeable outlet wherein the controller sends a control signal that closes the closeable inlet and a control signal that closes the closeable outlet whereby the chamber is isolated and batch sample mode conditions are created in the chamber;
    an electro-optical camera configured to view the water sample and produce an electronic signal from said view;
    an electronic circuit coupled to the camera configured to receive electronic information representing a plurality of time sequential optical images, wherein the information further comprises:
    a first image,
    a first image time,
    a second image, and
    a second image time; and
    a digital computer configured to process the information to calculate:
    an area and a perimeter of a suspended particle in the chamber;
    a first position of the suspended particle in the chamber using the first image wherein the first position further comprises a first horizontal position and a first vertical position;
    a second position of the suspended particle in the chamber using the second image wherein the second position further comprises a second horizontal position and a second vertical position;
    a perimeter of the suspended particle in the chamber using the first image or the second image;
    a vertical displacement of the suspended particle using the first vertical position and the second vertical position;
    a horizontal displacement of the suspended particle using the first horizontal position and the second horizontal position;
    a suspended particle velocity using the vertical displacement, the horizontal displacement, the first image time, and the second image time;
    a yes/no decision using the velocity and pre-defined criteria,
    a gravitational settling velocity using the yes/no decision and the velocity;
    a particle volume using the area and perimeter; and
    a density using the yes/no decision, the volume, the velocity, the density of water, and the viscosity of water.

16. A method for characterizing a floc particle in a water treatment facility, the method comprising:
    providing a sealable chamber that has a closeable inlet, a closeable outlet, and an electro-optical camera suitable for viewing suspended particles in the chamber;
    placing the chamber in the water of the treatment facility at a point downstream of a chemical introduction point;
    generating with the electro-optical camera a first signal responsive to a 2-dimensional projection of a suspended particle in a defined 3-dimensional region of the water;
    generating with the electro-optical camera a second signal responsive to a 2-dimensional projection of the suspended particle in the region;

calculating a time difference between the first signal and the second signal;

calculating a horizontal position difference of the suspended particle by comparing the horizontal position of the suspended particle from the first signal with the horizontal position of the suspended particle from the second signal;

calculating a vertical position difference of the suspended particle by comparing the vertical position of the suspended particle from the first signal with the vertical position of the suspended particle from the second signal;

calculating a settling velocity from the time difference and the vertical position difference;

calculating an area and perimeter of the suspended particle from one of the first signal or the second signal;

estimating a first volume of the suspended particle from the area and perimeter of the suspended particle;

calculating a density from the first volume, the settling velocity, the density of water, and the viscosity of water.

17. The method of claim 16, further comprising using said optical camera to view the water in a side stream.

18. The method of claim 16, wherein estimating further comprises using a method selected from the group of:
Circumscribed,
Heywood
Pappus,
Hydraulic, or
Heywood-Hydraulic.

19. The method of claim 16, wherein providing further comprises providing a turbulence-controlling element wherein:
the turbulence controlling element further comprises a mixer;

the method further comprises the following steps prior to generating a first signal:
opening the closable inlet and the closeable outlet;
closing the closeable inlet and the closeable outlet to collect a sample of liquid in the chamber;
operating the mixer; and
turning the mixer off;

the method further comprises the following steps after the step of estimating a first volume:
operating the mixer;
turning the mixer off;
generating with the electro-optical camera a third signal responsive to a 2-dimensional projection of a second suspended particle in a defined 3-dimensional region of the water;
calculating an area and perimeter of the second suspended particle from the third signal;
estimating a second volume of the second suspended particle from the area and perimeter of the second suspended particle;
comprising the first volume estimate to the second volume estimate to determine floc growth.

20. The method of claim 16, further comprising the step using a particle characteristic for providing real-time feedback to the process control system for the water treatment process.

21. The method of claim 16, further comprising the step of using a particle characteristic for generating a map of water treatment process response to one of:
a change of a chemical dose or
a change of a mixing parameter.

* * * * *